United States Patent [19]
Hughes

[11] Patent Number: 5,962,027
[45] Date of Patent: Oct. 5, 1999

[54] RETINAL CELL TRANSPLANT

[75] Inventor: Stephen E. Hughes, Delmar, N.Y.

[73] Assignee: Photogenesis, Inc., Los Angeles, Calif.

[21] Appl. No.: 08/322,735

[22] Filed: Oct. 13, 1994

Related U.S. Application Data

[63] Continuation of application No. 07/566,996, Aug. 13, 1990, abandoned, which is a continuation-in-part of application No. 07/394,377, Aug. 14, 1989, abandoned.

[51] Int. Cl.$^6$ .................................................. A61K 35/44
[52] U.S. Cl. ........................... 424/571; 424/422; 424/423; 424/427; 623/4; 623/5
[58] Field of Search ..................... 435/1, 240.2; 424/422, 424/423, 427, 428, 571; 623/4, 5

[56] References Cited

U.S. PATENT DOCUMENTS

| | | | |
|---|---|---|---|
| 3,394,591 | 7/1968 | Gleason | 128/305.5 |
| 4,014,342 | 3/1977 | Staub et al. | 128/305.1 |
| 4,304,866 | 12/1981 | Green et al. | 435/240 |
| 4,418,691 | 12/1983 | Yannas et al. | 128/156 |
| 4,495,288 | 1/1985 | Jarvis, Jr. et al. | 435/241 |
| 4,563,779 | 1/1986 | Kelman | 623/5 |
| 4,662,869 | 5/1987 | Wright | 604/22 |
| 4,665,774 | 5/1987 | Choyce | 623/5 |
| 4,689,399 | 8/1987 | Chu | 530/356 |
| 4,693,686 | 9/1987 | Sendax | 433/173 |
| 4,702,697 | 10/1987 | Linkow | 433/173 |
| 4,727,018 | 2/1988 | Eichner et al. | 435/1 |
| 4,868,116 | 9/1989 | Morgan et al. | 435/240.1 |
| 4,900,300 | 2/1990 | Lee | 604/22 |
| 4,927,676 | 5/1990 | Williams et al. | 428/36 |
| 4,940,468 | 7/1990 | Petillo | 606/170 |
| 4,963,489 | 10/1990 | Naughton et al. | 435/240.1 |
| 5,000,963 | 3/1991 | Hefton | 424/574 |
| 5,292,802 | 3/1994 | Rhee et al. | 525/541 |
| 5,308,889 | 5/1994 | Rhee et al. | 523/113 |
| 5,322,691 | 6/1994 | Darouger et al. | 424/427 |
| 5,323,788 | 6/1994 | Silvestrini et al. | 128/897 |
| 5,324,260 | 6/1994 | O'Neill et al. | 604/96 |
| 5,326,346 | 7/1994 | Cortes | 623/4 |
| 5,326,584 | 7/1994 | Kamel | 427/491 |
| 5,328,481 | 7/1994 | Wang | 604/506 |
| 5,342,370 | 8/1994 | Simon et al. | 606/107 |
| 5,374,515 | 12/1994 | Parenteau et al. | 435/1 |

FOREIGN PATENT DOCUMENTS

| | | |
|---|---|---|
| 0340698 A2 | 11/1989 | European Pat. Off. . |
| 0535506 A1 | 4/1993 | European Pat. Off. . |
| 90912685 | 2/1995 | European Pat. Off. . |
| 4004921 A1 | 8/1991 | Germany . |
| WO 91/02499 | 3/1991 | WIPO . |
| WO 92/08406 | 5/1992 | WIPO . |

OTHER PUBLICATIONS

Li, L. et al., Exp. Eye Res., vol. 47, pp. 771–785, 1988.
Sheedlo, H.J. et al., Exp. Eye Res., vol. 48, pp. 841–854, 1989.
Lopez, R. et al., Investigative Ophthalmology & Visual Science, vol. 30(3), pp. 586–588, Mar. 1989.
Silverman, M.S. et al., Investigative Ophthalmology & Visual Science, vol. 30(8), pp. 1684–1690, Aug. 1989.
Maurice, D.M. et al., ARVO Abstracts—Supplement to Investigative Ophthalmology & Visual Science, p. 10, abstract #9, Apr. 1979.
Silverman, M.S. et al., Inherited & Environmentally Induced Retinal Degenerations, Alan R. Liss, Inc., pp. 687–704, 1989.
Silverman, M.S. et al., Supplement to Investigative Ophthalmology & Visual Science, vol. 31, p. 594, abstract #2909–7, 1990.
Department of Health and Human Services Grant Application, "Transplantation of Mammalian Photoreceptors", Martin S. Silverman, pp. 1–61, submitted May, 1987, funded by NEI Feb. 16, 1988, Grant No. 1R01 EY07547–01.
Department of Health and Human Services Grant Application, Transplantation of Mammalian Photoreceptors, Martin S. Silverman, pp. 1–13, submitted May, 1986, funded by NEI Sep. 11, 1986, Grant No. 1 RO3 EY 06943–01.
Silverman et al., "Transplantation of retinal photoreceptors to light damaged retina: Survival and integration of receptors from a range of postnatal ages", Soc. Neurosci. Abstr. 17:1301, 1987.
Hughes et al., "Transplantation of Retinal Photoreceptors to Dystrophic Retina", Society Neuro Sci Abstr. 1277, Nov. 1988.
Silverman et al., "Transplantation of Human Photoreceptors to Light Damaged Retina", Soc. Neurosci. Abstr., 18:1278 (1988).
Silverman et al., "Light Dependent Activation of Light Damaged Retina by Transplanted Photoreceptors", Suppl., Invest. Ophthalmol. Visual Sci., 30:208, (1989).
Silverman et al., "Transplantation of Photoreceptors to Light Damaged Retina", Invest. Ophthalmol. Vis. Sci., vol. 30, No. 8, 1684–1690, Aug. 1989.
Silverman et al., "Transplantation of Human and Non–Human Primate Photoreceptors to Damaged Primate Retina", Invest. Ophthalmol. Visual Sci., 31:594, 1990.
Valentino et al., "Photoreceptor rescue in RCS rat and rd mouse by heat shock", Suppl., Invest. Ophthalmol. Vis. Sci., 31:594, 1990.
Hughes et al., "Transplanted Photoreceptors Form Synapses in Light–Damaged Retina", Suppl. Invest. Ophthalmol. Vis. Sci. 31:594, 1990.
Weiss, "Transplanting the Light Fantastic Cells from eye donors may someday restore vision in some blind individuals" Science News, vol. 136, No. 19, pp. 297–300, Nov. 4, 1989.

(List continued on next page.)

Primary Examiner—Jean C. Witz
Attorney, Agent, or Firm—Daniel B. Schein, Esq.

[57] ABSTRACT

Surgical instruments, surgical techniques, grafts, cell and tissue isolation techniques, and a method for transplanting retinal cells, including photoreceptors, retinal pigment epithelium, and choroidea within their normal configuration, or all three tissues in a co-transplantation procedure are provided.

15 Claims, 13 Drawing Sheets

OTHER PUBLICATIONS

Shiosaka et al., "A simple method for the separation of retinal sublayers from the entire retina with special reference to application for cell culture", Jour. Neurosci. Methods, 10:229–235 (1984).

Sarthy et al., "Isolated cells from a mammalian retina", Brain Research, 176:208–212 (1979).

Lopez et al., "Transplanted Retinal Pigment Epithelium Modifies the Retinal Degeneration in the RCS Rat", Invest. Ophthalmol. Vis. Sci., 30:586–589.

Li et al., "Transplantation of Retinal Pigment Epithelial Cells to Immature and Adult Rat Hosts: Short—and Long–term Survival Characteristics", Exp. Eye Res. 47:771–785 (1988).

Li et al., "Inherited Retinal Dystrophy in the RCS Rat: Prevention of Photoreceptor Degeneration by Pigment Epithelial Cell Transplantation", Exp. Eye Res. 47:911–917 (1988).

Sheedlo et al., "Functional and Structural Characteristics of Photoreceptor Cells Rescued in RPE–cell Grafted Retinas of RCS Dystrophic Rats", Exp. Eye Res. 48:841–854 (1989).

Mac Leish et al., "Growth and Synapse Formation Among Major Classes of Adult Salamander Retinal Neurons In Vitro", Neuron, vol. 1, 751–760, Oct. 1988.

Townes–Anderson et al., "Rod Photoreceptors Dissociated From the Adult Rabbit Retina", Jour. of Neuroscience, vol. 8, No. 1, pp. 320–331, Jan. 1988.

Politi et al., "Generation of Enriched Populations of Cultured Photoreceptor Cells", Invest. Ophthalmol. Vis. Sci. vol. 27, No. 5, pp. 656–665, May 1986.

Del Cerro, "Retinal Transplants" Progress in Retinal Research vol. 9, pp. 229–269.

Klassen et al., "Retinal transplants can drive a pupillary reflex in host rat brains", Proc. Natl. Acad. Sci. U.S.A. vol. 84, pp. 6958–6960, Oct. 1987.

Klassen et al., "Anatomical and Behavioral Correlates of a Xenograft–Mediated Pupillary Reflex", Experimental Neurology 102, 102–108, (1988).

del Cerro et al., "Intraretinal transplantation of fluorescently labeled retinal cell suspensions", Neurosci. Lt., 92 pp. 21–26, (1988).

del Cerro et al., "Intraocular Retinal Transplants", Invest. Ophthalmol. Vis. Sci., vol. 26, pp. 1182–1185, Aug. 1985.

Anderson et al., "Retinal Detachment in the Cat: The Pigment Epithelial–Photoreceptor Interface", Invest. Ophthalmol. Vis. Sci. vol. 24, pp. 906–926, Jul. 1983.

Bignami et al., "The Radial Glia of Muller in the Rat Retina and Their Response to Injury, An Immunofluorescence Study with Antibodies to the Glial Fibrillary Acidic (GFA) Protein", Exp. Eye Res., 28: 63–69, (1979).

Hicks et al., "Different Rhodopsin Monoclonal Antibodies Reveal Different Binding Patterns on Developing and Adult Rat Retina", Jour. of Histochemistry & Cytochemistry, vol. 35, No. 11, pp. 1317–1328, (1987).

Honig et al., "Fluorescent Carbocyanine Dyes Allow Living Neurons of Identified Origin to be Studied in Long–term Cultures", Jour. of Cell Biology, 103:171–187, Jul. 1986.

Mayerson et al., "An Improved Method for Isolation and Culture of Rat Retinal Pigment Epithelial Cells", Invest. Ophthalmol. & Vis. Sci., 26:1599–1609, Nov. 1985.

McConnell et al., "Regeneration of ganglion cell axons in the adult mouse retina", Brain Research, 241:362–365 (1982).

Mollenhauer, "Plastic Embedding Mixtures for Use in Electron Microscopy", Stain Tech., 39:111–114.

O'Steen, "Retinal and Optic Nerve Serotonin and Retianl Degeneration as Influenced by Photoperiod", Exp. Neurology, 27:194–205, (1970).

Pu et al., "Biochemical Interruption of Membrane Phospholipid Renewal in Retinal Photoreceptor Cells", Jour. of Neurosci., vol. 4, No. 6, pp. 1559–1576, Jun. 1984.

Royo et al., "Retinal Transplantation from Fetal to Maternal Mammalian Eye", Growth, 23:313–336, (1959).

Simmons et al., "Physiological Responses in Retianl Transplants and Host Tecta Evoked By Electrical or Photic Stimulation of Transplanted Embryonic Retinae", Soc. Neurosci. Abstr. 10:668, (1984).

Sokoloff et al., "The [C]Deoxyglucose Method for the Measurement of Local Cerebral Glucose Utilization: Theory, Procedure, and Normal Values in the Conscious and Anesthetized Albino Rat", Jour. of Neuorchem. 28:897–916, (1977).

Turner et al., "Newborn Rat Retinal Cells Transplanted Into a Retinal Lesion Site in Adult Host Eyes", Develop. Brain Research, 26:91–104, (1986).

Bjorklund et al., "Neural Grafting in the Mammalian CNS", Elsevier Science Publishing B.V., Netherlands, Ch. 38, pp. 431–436.

LaVail et al., "Histotypic Organization of the Rat Retina in Vitro", Z. Zellforsch, Springer Verlag, 114:557–579 (1971).

Osborne, N. and Chader, G., Eds., *Progress In Retinal Research*, vol. 9, Chapter 6, Pergamon Press, Elmsford, New York (1990).

Gouras, et al., "Reconstruction of Degenerate rd Mouse Retina By Transplantation Of Transgenic Photoreceptors," *Investigative Ophthalmology & Visual Science,* vol. 33/9, Aug. 1992, pp. 2579–2586.

Silverman, et al., "Photoreceptor Transplantation; Anatomic, Electrophysiologic, and Behavioral Evidence For The Functional Reconstruction Of Retinas Lacking Photoreceptors," *Experimental Neurology,* 115, 87–94 (1992).

Li et al., "Optimal Conditions For Long–term Photoreceptor Cell Rescue In RCS Rats; The Necessity For Healthy RPE Transplants," *Exp. Eye Res.,* 52:669–679 (1991).

Powell et al., "Controlled Release Of Nerve Growth Factor From A Polymeric Implant," *Brain Res.,* 515:309–311 (1990).

Lane et al., "Transplantation Of Retinal Pigment Epithelium Using A Pars Plana Approach," *Eye,* 3:27–32 (1989).

Newsome et al., "Transplantation Of Human Retinal Pigment Epithelium Into Primate Model of Macular Degeneration," Retina Society Meeting, Toronto, Canada Sep. 1991.

Wilchek et al., "Immobilization Of Enzymes And Affinity Ligands Onto Agarose Via Stable And Uncharged Carbamate Linkages," *Biochem. Int'l.,* vol. 4, No. 6, pp. 629–635, Jun. 1982.

Kitchell et al., "Poly(lactic/glycolic acid) Biodegradable Drug–Polymer Matrix Systems," *Methods In Enzymology,* 112:436–448 (1985).

"Biodegradable Polymers," Polysciences, Inc. Data Sheet #365, Jan. 1990.

Pfeffer, "Improved Methodology For Cell Culture Of Human And Monkey Retinal Pigment Epithelium," *Progress In Retinal Research,* vol. 10, Chapter 10, pp. 251–291 (1991).

Cuatrecasas et al., "Selective Enzyme Purification By Affinity Chromatography," *Biochem.,* 61:636–643 (1968).

Axen et al., "Chemical Coupling Of Peptides And Proteins To Polysaccharides By Means Of Cyanogen Halides," *Nature*, 214:1302–1304, Jun. 24, 1967.

Wise et al., "Lactic/Glycolic Acid Polymers," *Drug Carriers In Biology And Medicine*, Ed.: Gregorias, Chapter 12, pp. 237–270 (1979).

LaVail et al., "Multiple Growth Factors, Cytokines, and Neurotrophins Rescue Photoreceptors From The Damaging Effects Of Constant Light," *Proc. Nat'l Acad. Sci.*, USA, vol. 89, pp. 11249–11253 (1992).

Faktorovich et al., "Basic Fibroblast Growth Factor and Local Injury Protect Photoreceptors From Light Damage In The Rat," *Journal Of Neuroscience*, 12(9):3554–3567, Sep. 1992.

Faktorovich et al., "Photoreceptor Degeneration In Inherited Retinal Dystrophy Delayed By Basic Fibroblast Growth Factor," *Nature*, vol. 347, pp. 83–86, Sep. 6, 1990.

Silverman et al., "Rescue Of Host Cones By Transplanted Donor Photoreceptors In The rd Mouse," *Invest. Ophth. & Vis. Sci.*, vol. 34, No. 4, ARVO Abstract No. 1937–93, Mar. 15, 1993.

Fang et al., "Development Of A Surgical Procedure And Instrument For Transplantation Of Extended Gelatin Sheets For The Subretinal Space," *Invest. Ophth. & Vis. Sci.*, 34:1093 (1993).

Silverman et al., "Photoreceptor Transplantation In Inherited And Environmentally Induced Retinal Degeneration: Anatomy, Immunohistochemistry, And Function," *Inherited & Environmentally Induced Retinal Degenerations*, Alan R. Liss, Inc. pp. 687–704 (1989).

Silverman, "Department of Health and Human Services Grant Application, Transplantation of Mammalian Photoreceptors", Martin S. Sivlerman, pp. 1–13, submitted May, 1986, funded by NEI Sep. 11, 1986, Grant No. IRO3 EY 06943–01.

Silverman, "Department of Health and Human Services Grant Application, Transplantation of Mammalian Photoreceptors", Martin S. Silverman, pp. 1–61, submitted May, 1987, funded by NEI Feb. 16, 1988, Grant No. IRO1 EY07547–01.

Silverman, Transplantation of retinal photoreceptors to light damaged retina: Survival and integration of receptors from a range of postnatal ages, Soc. Neurosci. Abstr. 17:1301, abs. #360.17, 1987.

Silverman, "Transplantation of Photoreceptors to Light Damaged Retina", Invest. Ophthalmol. Vis. Sci., vol. 30, No. 8, 1684–1690, Aug. 1989.

Silverman, Light Dependent Activation of Light Damaged Retina by Transplanted Photoreceptors, Suppl., Invest. Ophthalmol., Visual Sci., 30:208, abs. # 9, 1989.

Silverman, "Transplantation of Human and Non–Human Primate Photoreceptors to Damaged Primate Retina", Invest. Ophthalmol. Visual Sci., 31:594, abs # 2909–7, 1990.

Silverman, "Photoreceptor transplantation to dystrophic retina. Retinal Degeneration", (ed. Anderson R.E., LaVail, MM, and Hollyfield J.G.). CRC Press, Inc., Boca Raton, Florida, pp. 321–335, Chapter 29, 1991.

Silverman, Effect of Genetic Disparity on Photoreceptor Transplant Survival, Suppl., Invest. Ophthalmol. Vis. Sci. 32:983, abs # 1549.

Silverman, "A comparison of Ocular Dominance Patterns in Cat and Monkey", Suppl. Invest. Ophthalmol. Visual Sci. 22:12 # 3, abs. # 13, Mar. 1982.

Simmons, "Physiological Responses in Retinal Transplants and Host Tecta Evoked by Electrical or Photic Stimulation of Transplanted Embryonic Retinae", Soc. Neurosci. Abstr. 10:668, abs # 196.5.

Sokoloff, "the [C]Deoxyglucosel Method for the Measurement of Local Cerebral Glucose Utilization: Theory, Procedure, and Normal Values in the Conscious and Anesthetized Albino Rat", Jour. of Neurochem., 28:897–916, 1977.

Tootell, "Color–Dependent Deoxyglucose Patterns Within Macaque Cortex", Arvo Abstracts 226, Suppl., Invest. Ophthalmol. Vis. Sci. pp. 226, abs # 12, Apr. 1980.

Townes, "Rod Photoreceptors Dissociated from the Adult Rabbit Retina", Jour. of Neuroscience, vol. 8, No. 1, pp. 320–331, Jan., 1988.

Turner, "Newborn Rat Retinal Cells Transplanted Into a Retinal Lesion Site In Adult Host Eyes", Develop. Brain Research, 26:91–104, (1986).

Valentino, "Photoreceptor rescue in RCS rat and rd mouse by heat shock", Suppl. Invest. Ophthalmol. Vis. Sci., 31:594, abs. # 2911–9, 1990.

Weiss, Transplanting the Light Fantastic Cells from eye donors may someday restore vision in some blind individuals, Science News, vol. 136, No. 19, pp. 297–300, Nov. 4, 1989.

del Cerro; "Intraocular Retinal Transplants", Invest. Ophthalmol, Vis. Sci., vol. 26, pp. 1182–1185, Aug. 1985.

del Cerro; "Intraretinal transplantation of fluorescently labeled retinal cell suspensions", Neurosci. Lt., 92 pp. 21–26, (1988).

N. Bhatt; "Transplantation of Human Retinal Pigment Epithelial Cells Into Rabbits", *Invest. Opthal. Vis. Sci.*, 34:#4 abs # 1920–76 Mar. 1993.

A. Bonds; "Visually Evoked Potentials and Deoxyglucose Studies of Monocularly Deprived Cats", *Suppl., Invest. Opthal. Vis. Sci.*, 18: 1980 Apr. abs #11 p. 225 only.

D. Cameron; "The Cone Photoreceptor Mosaic of the Green Sunfish", *Soc. Neuroscience*, abs #352.6 part 1 18:838, 1992.

P. Custis; "Clinical Angiographic and Histopathologic Correlations in Surgically Removed Subfoveal Choroidal Neovascularization", *Invest. Opthal. Vis. Sci.*, 34:834, 1993 #4 Mar. abs #651.

M. del Cerro; "Selective Transplantation of Enriched Cell Populations Derived from Immature Rat Retina", *Suppl. Invest. Opthal. Vis. Sci.*, 30:208, 1989 abs #6.

L. Del Priore; "Transplantation of Retinal Pigment Epithelium (RPE) Onto Bruch's Membrane in Organ Culture", *Suppl. Invest. Opthal. Vis. Sci.*, 33:1127, 1992 abs #2174.

L. Del Priore; "Experimental and Surgical Aspects of Retinal Pigment Epithelial Cell Transplantation", *Eur. J. Implant Ref. Surg.*, 5:128:131, 1993 Jun.

L. Del Priore; "Differential Ability of Aged Versus Young Human Bruch's Membrane to Support Repopulation By Healthy RPE", *Invest. Opthal. Vis. Sci.*, 34:834, #4 1993 Mar. abs #652.

J. Du; "Long Term Survivalof Infant Versus Adult Photoreceptor Transplants Labeled by Tritiated Thymidine", *Suppl., Invest. Opthal. Vis. Sci.*, 32:983, 1991 abs #1546.

J. Du; "Neonatal Mouse Photoreceptor Transplants Replace the Photoreceptor Layer of the Host", *Invest. Opthal. Vis. Sci.*, #4 34:1096, 1993 Mar abs #1934.

S. Edwards; "Light–Regulated Portein Phosphatase Activity in Limulus Ventral Photoreceptors", *Soc. Neuroscience*, 16:405, 1990 abs #171.6.

O. Ferguson; "Effect of Genetic Disparity on Photoreceptor Transplant Survival", *Invest. Opthal. Vis. Sci.,* 32:983, 1991 Mar. abs #1549.

A. Adolph; "Function and Structure in Isolated Subretinal Transplants", *Invest. Opthal. Vis. Sci.,* 34:1096, Mar. 1993 abs #1933.89 #4.

R. Aramant; "Xenografting Human Fetal Retina to Adult Rat Retina", *Suppl., Invest. Opthal. Vis. Sci.,* 31:594, 1990 abs #2907–5.

R. Aramant; "The Fate of Retinal Ganglion Cells, Retrogradely Labelled with Fluorogold and Transplanted to Rat Retina", *Suppl. Invest. Opthal. Vis. Sci.,* 32:983, 1991 abs #1545.

R. Aramant; "Tracing of Connections Between Retinal Transplants and Host Retina with Dil", *Invest. Opthal. Vis. Sci.,* #4 34:1096, 1993 Mar. abs #1935–91.

ARVO "Abstract Packet for Annual Meeting" Sarasota, Florida (May 2–May 7, 1993).

ARVO "Conference Brochure for Annual Meeting" Sarasota, Florida (May 2–May 7, 1993).

H. Kaplan; "Retinal Pigment Epithelium Regeneration in the Non–Human Primate", *Suppl., Invest. Opthal. Vis. Sci,* 33:1127, 1992 abs #2173.

J. Kordower; "Fetal Monkey Retina Transplanted into Adult Rat Eyes", *Suppl. Invest. Opthal. Vis. Sci.,* 30:208, 1989 abs #7.

B. Kruszewska; "Ultrastructure and Transduction in the Caudal Photoreceptor of Crayfish", *Soc. Neuroscience,* 16:405, 1990 abs #171.5.

M. LaVail; "RPE Cell Transplantation in RCS Rats: Normal Metabolism in Rescued Photoreceptors", *Suppl., Invest. Opthal. Vis. Sci.,* 33:1127, 1992 abs #2176.

J. Lee; "Transplantation of Cultured Retinal Pigment Epithelium to Rabbit Retina Injured by Sodium Iodate", *Suppl. Invest. Opthal. Vis. Sci.,* 33:1127, 1992 abs #2175.

Y. Liu, "Photoreceptors Inner and Outer Segments in Transplanted Retina", *Soc. Neuroscience,* abs #171.1 16:405, 1990.

Y. Liu; "Transplantation of Confluent Sheets of Adult Human RPE", *Invest. Opthal. Vis. Sci.,* abs #2180 33:1128, 1992 Mar.

Y. Liu; "Transplantation of Confluent Sheets of Adult Human and Rat RPE on a Thin Substrate", *Invest. Opthal. Vis. Sci.,* 34:1112, 1993 abs #2018.

R. Lopez; "Transplantation of Human RPE Cells into the Monkey", *Suppl., Invest. Opthal. Vis. Sci.,* 31:594, 1990 abs #2910–8.

R. Lund; "Axonal Outgrowth from Transplanted Retinae is Stimulated by Appropriate Target Regions", Arvo Abstracts 288.

J. Maurice "Keratoplasty with Cultured Endothelium on Thin Membranes," *ARVO Abstracts, Suppl., Invest. Opthal. Vis. Sci.,* Apr. 1979 p. 10 abs #9.

J. McCulley; "Corneal Endothelial Transplantation" Ophthalmology, vol. 87 #3 pp. 194–201 Mar. 1980.

S. Hughes; "Whole Cell Recordings of Isolated Retinal Pigment Epithelial Cells of the Frog", *Soc. Neuroscience Abstr.,* 17:1301, 1987.

S. Hughes; "Differential Survival of Sensory Elements in Intracranial Otic Transplants", *Soc. Neuroscience,* 17:1138, 1991 part 2 abs #452.12.

S. Hughes; "Quantification of Synapses in Light–Damaged Retina Reconstructed by Transplantation of Photoreceptors", *Invest. Opthal. Vis. Sci.,* 33:1058, #4 1992 Mar. abs. #1832–3.

S. Hughes; "Explorations of Otic Transplantation", *Experimental Neurology,* 115:37–43, 1992.

G. Jacobs; "An Ultraviolet–Sensitive Cone in the Gerbil Retina", *Soc. Neuroscience,* 18:838, 1992 part 1 abs #352.1.

L. Jiang; "Intraocular Retinal Transplantation in Retinal Degeneration (rd/rd) Murine Strains", *Suppl., Invest. Opthal. Vis. Sci.,* 30:208, 1989.

O. Fischer; "Photoreceptor Topography in the Retinae of Anubis Baboons", *Soc. Neuroscience,* 18:838 1992 part I abs #352.7.

C. Garcia; "Comparison of Allogeneic and Syngeneic RPE Transplants in Renal Subcapsular Space", *Invest. Opthal. Vis. Sci.,* 34:1112, 1993 abs #2017–49.

E. Gao; "Low Immunogenicity of Neonatal Murine Photoreceptor Cells for Cytotoxic T Lymphocytes in Mice", *Invest. Opthal. Vis. Sci.,* 33:1285, 1992 #4 abs #296.3.

M. Gelanze; "Survival of Photoreceptors Transplanted to the Subretinal Space of Adult RCS Rats", *Suppl. Invest. Opthal. Vis. Sci.,* 30:208, 1989 abs #8.

P. Gouras; "Transplanted Photoreceptors Form Mature Outer Segments in Degenerate rd Mouse Retina", *Opthal. Invest. Vis. Sci.,* 33:1128, 1992 #4 Mar. abs #2181.

P. Gouras; "Anatomy and Physiology of Photoreceptor Transplants in Degenerate C3H Mouse Retina", *Invest. Opthal. Vis. Sci.,* 34:1096, 1993 #4 Mar. abs #1938–94.

Silverman et al, Current Eye Research, 9(2), pp. 183–192 (1990).

Radtke et al, Graefe's Arch. Clin. Exp. Ophthalmo. vol. 224, pp. 230–233 (1986).

M.M. Jumblatt et al. "A Gelatin Membrane Substrate for the Transplantation of Tissue Cultured Cells", *Transplantation,* vol. 29, No. 6, pp. 498–499, Jun. 1980.

T. Moritera; Transplants of Monolayer Retinal Pigment Epithelium Grown on Biodegradable Membrane in Rabbits, *Invest. Opthal. Vis. Sci.,* 34: 1993 #4 Mar. abs #1919–75.

J. Muller; "Morphology and Synaptic Inputs to Lucifer Yellow Injected Bipolar Cells In Rat Retinal Slices", *Soc. Neuroscience,* 17:1013, 1991 pt 2 abs 403.4.

J. Muller; "Rod and Cone Inputs to Bipolar Cells in the Rat Retina.", Mar. 1993 Invest. Opth. Vis. Sci. 34:1013, #4 abs #.

K. Mueller; "Autotransplantation of Retinal Pigment Epithelium in Intravitreal Diffusion Chamber", *Retinal Pigment Epithelium,* Part II, vol. 80, No. 3, pp. 530–537 1993.

M. Nasir; "Choriocapillaris Atrophy as a Complication of Surgical Excision of Choroidal Neovascular Membranes", *Invest. Opthal. Vis. Sci.,* 34:834, 1993 Mar. #4 abs #653.

H. Petry; "Immunocytochemical Identification of Photoreceptor Populations in the Retinas of Normal and Red–Light–Reared Tree Shrews", *Soc. Neuroscience,* 18:838, 1992 abs #352.9.

J. Radel; "Quantification of Light–Activated Pupilloconstriction in Rats Mediated by Intracranially Transplanted Retinae", *Suppl., Invest. Opthal. Vis. Sci.,* 32:983, 1991 abs #1550.

S. Schuschereba; "Retinal Cell and Photoreceptor Transplantation Between Adult New Zealand Red Rabbit Retina", *Experimental Neurology,* 115:95–99, 1992.

A. Seaton; "Inhibition of Neovascularization by the Transplantation of Healthy Retinal Pigment Epithelial Cells into the RCS Rat", *Suppl., Invest. Opthal. Vis. Sci.,* 32:983, 1991 abs #1547.

H. Sheedlo; "Photoreceptor Cell Rescue by REP–Cell Grafts in RCS Rats at Early and Late Stages of Retinal Dystrophy", *Suppl., Invest. Opthal. Vis. Sci.,* 30:208, 1989 abs #10.

M. Silverman; "Deoxyglucose Mapping of Orientation and Spatial Frequency in Cat Visual Cortex", *Suppl. Invest. Opthal. Vis. Sci.,* 18, 1980 Apr. p. 225 Abs #10.

M. Silverman; "Deoxyglucose Mapping of Orientation in Cat Visual Cortex", *Recent Advances in Vision, Optical Society of America Technical Digest,* SA13, 1980.

M. Silverman; "The Retinotopic Organization of Cat Striate Cortex.", *Suppl., Invest. Opthal. Vis. Sci.,* 22:105, 1982 abs #1.

M. Silverman; "Photoreceptor Rescue in the RCS Rat Without Pigment Epithelial Transplantation", *Soc. Neuroscience,* 15:115, 1989 Nov. abs #51.1.

M. Silverman; "Photoreceptor Transplantation to Dystrophic Retina", *Retinal Degenerations* (ed. by R. Anderson,) CRC Press, Inc. Ch. 29, pp. 321–335, 1991.

M. Silverman; "Restoration of the Pupillary Reflex by Photoreceptor Transplantation", *Suppl. Invest. Opthal. Vis. Sci.,* 32:983, 1991 abs #1548.

M. Silverman; "Photoreceptor Transplantation: Anatomic Electrophysiologic and Behavorial Evidence for the Functional Reconstruction of Retinas Lacking Photoreceptors", *Soc. Neuroscience,* 17:12, 1991.

M. Silverman; "Transplantation of Retinal Photoreceptors to Light–Damaged Retina", Suppl. Invest. Ophthalmol Vis. Sci., vol. 288, 1987.

T. Solomons; Graham –"Special Topic M Photochemistry of Vision", *Organic Chemistry,* 5th ed., John Wiley & Sons, Inc., pp. 1168–1171.

L. Tien; "In Search of A Receptor for Outer Segments in Rat Retinal Pigmented Epithelium", *Soc. Neuroscience,* 16:405, 1990 abs #171.3.

R. Tootell; "Deoxyglucose Mapping of Color and Spatial Frequency Organization in Monkey and Cat Cortex", *Recent Advances in Vision, Optical Society of America Tech. Digest.,* SA14, 1980.

R. Tootell; "2DG Study of Retinotopic Organization in Macaque Striate Cortex", *Suppl. Invest. Ophthal. Vis. Sci.,* 22:12, 1982 #3 Mar. abs #14.

R. Tootell; "Deoxyglucose Analysis of Retinotopic Organization in Primate Striate Cortex", *Science,* 218:902–904, 1982 Nov.

R. Tootell; "Two Methods for Flat–Mounting Cortical Tissue", *J. Neurosci. Methods,* 15:177–190, 1985.

B. Tuliusson; "Reversed Ratio of Color Specific Cones in Rabbit Retinal Transplants", *Invest. Opthal. Vis. Sci.,* #4 34:1096, 1993 Mar. abs #1936–92.

T. Valentino; "Transplanted Photoreceptors Form Synapses in Reconstructed RCS Rat Retina", *Soc. Neuroscience* 16:405, 1990 abs #171.2.

T. Valentino; "Photoreceptor Sheets Isolated from the Neonatal Rat Retina Lack Synapses and Other Retinal Cells", *Soc. Neuroscience,* 18:838, 1992 abs #352.8.

S. Vinores; "Ultrastructural Localization of RPE Epitopes in In Situ and Clutrued RPE Cells and their Expression in Fibroblasts in Vitreous Culture", *Soc. Neuroscience,* 16:405, 1990 abs #171.4.

C. Zucker; "Synaptic Microcircuitry of Rat Retinal Transplants Ultrastructural Observations", *Suppl. Invest. Opthal. Vis. Sci.,* 31:594, 1990 abs #2906–4.

Anderson; "Retinal Detachment in the Cat; The Pigment Epithelial–Photoreceptor Interface", Invest. Ophthalmol. Vis. Schi., vol. 24, pp. 906–926, Jul. 1983.

Aramant; "Tracing of connections Between Rectinal Transplants and Host Retina with . . . ", Invest. Ophthalmol. Vis. Sci., 34:1096, #4, abs. #1935–91, Mar. 15, 1993.

del Cerro, "Retinal Transplants", Progress in Retinal Research vol. 9, chapter 6, pp. 229–269, 1990.

Gouras, "Anatomy and Physiology of Photoreceptor Transplants in Degenerate C3H Mouse Retina", Invest. Opthalmol. Vis. Sci. 34:1096, #4, abs. #1938–94, Mar. 15, 1993.

Hughes, "Transplantation of Retinal Photoreceptors to Dystrophic Retina", Society Sci. Abstr. 1277, abs. #511–16, Nov. 1988.

Hughes, "Transplanted Photoreceptors Form Synapses in Light–Damaged Retina", Suppl. Invest. Ophthalmol. Vis. Sci., 31:594, abs. #2908–6, 1990.

Klassen, "Retinal transplants can drive a pupillary reflex in host rat brains", Proc. Natl. Acad. Sci. U.S.A., vol. 84, pp. 6958–6960, Oct. 1987.

Klassen, "Anatomical and Behavioral Correlates of a Xenograft–Mediated Pupillary Reflex", Experimental Neurology 102, 102–108, (1988).

McConnell, "Regeneration of ganglion cell axons in the adult mouse retina", Brain Research, 241:362–365 (1982).

Mollenhauer, "Plastic Embedding Mixtures for use in Electron Microscopy", Stain Tech., 39:111–114.

O'Steen, Retinal and Optic Nerve Serotonin and Retinal Degeneration as Influenced by Photoperiod, Exp. Neurology, 27:194–205, 1970.

Politi, Generation of Enriched Populations of Cultured Photoreceptor Cells, Invest. Ophthalmol. Vis. Sci., vol. 27, No. 5, pp. 656–665, May, 1986.

Pu, "Biochemical Interruption of Membrane Phospholipid Renewal in retinal Photoreceptor Cells", Jour. of Neurosci., vol. 4, No. 6, pp. 1559–1576, Jun. 1984.

Raymond, "Progenitor Cells in Outer Nuclear Layer of Goldfish Retina That Normally Produce Only Rods Produce other Neurons during Retinal Degeneration", Suppl., Invest. Ophthalmol. Vis. Sci. 28:288, abs #13, 1987.

Royo, "Retinal Transplantation from Fetal to Maternal Mammalian Eye", Growth, 23:313–336, 1959.

Sarthy, Isolated Cells from a Mammalian Retina, Brain Research, 176:208–212, 1979.

Sheedlo, "Functional and Structural Characteristics of Photoreceptor Cells Rescued in RPE–cell Grafted Retinas of RCS Dystrophic Rats", 48:841–854, 1989 Exp. Eye Res.

Shiosaka, "A simple method for the separation of retinal sublayers from the entire retina with special reference to application for cell culture", Jour. Neurosci. Methods, 10:229–235, 1984.

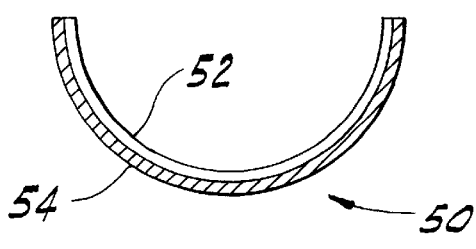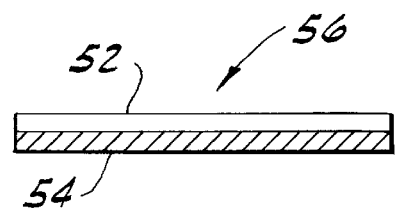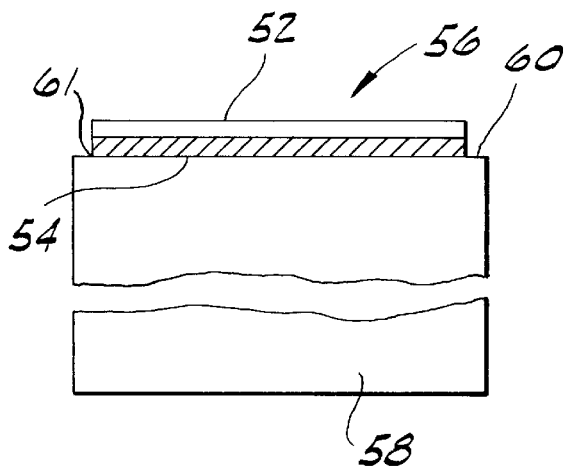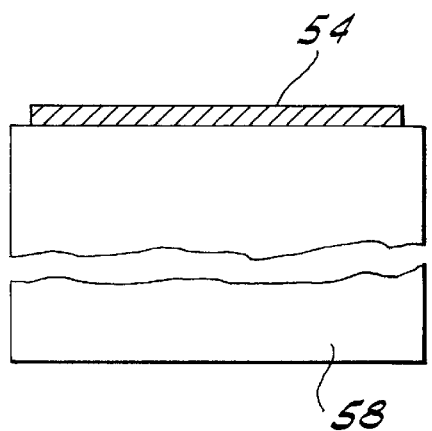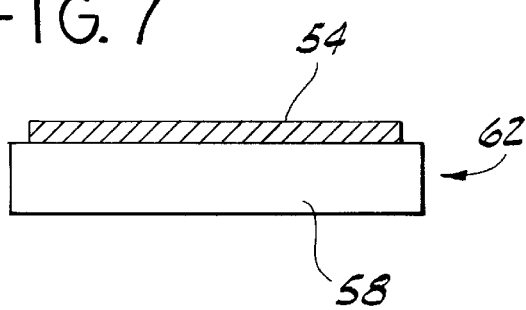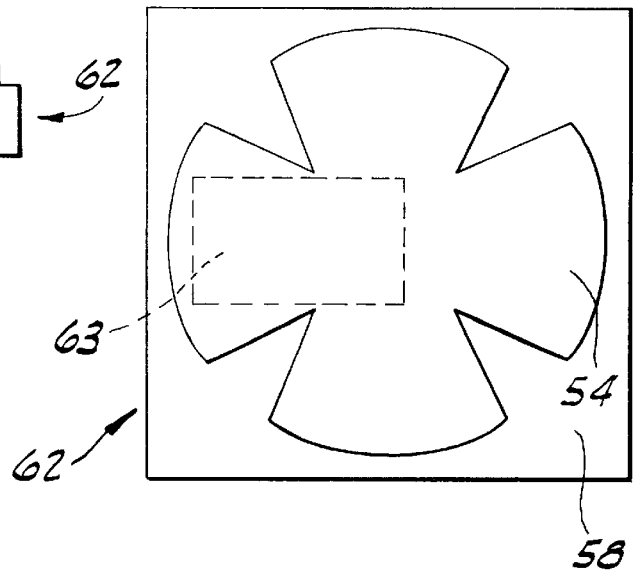

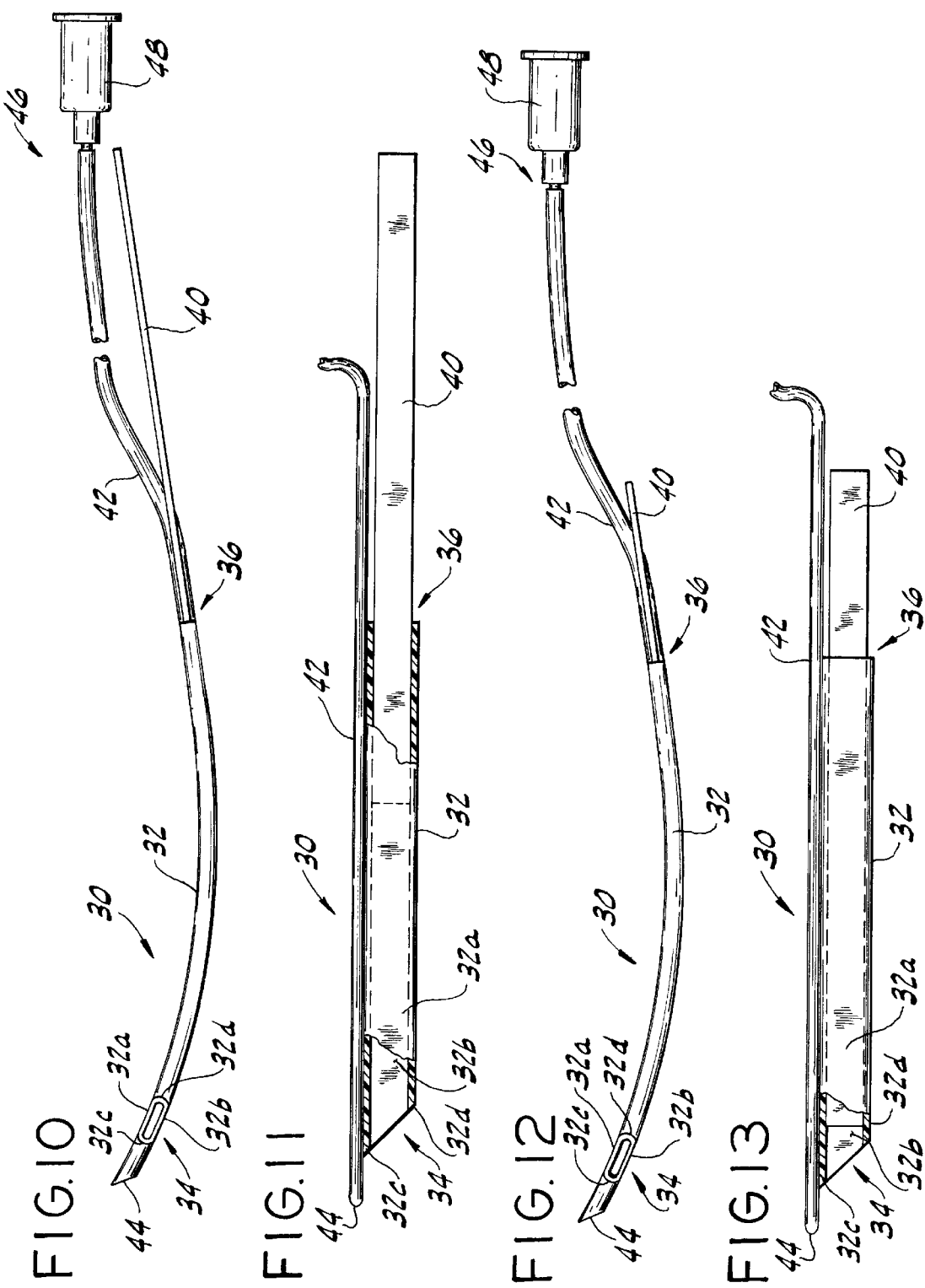

FIG. 24
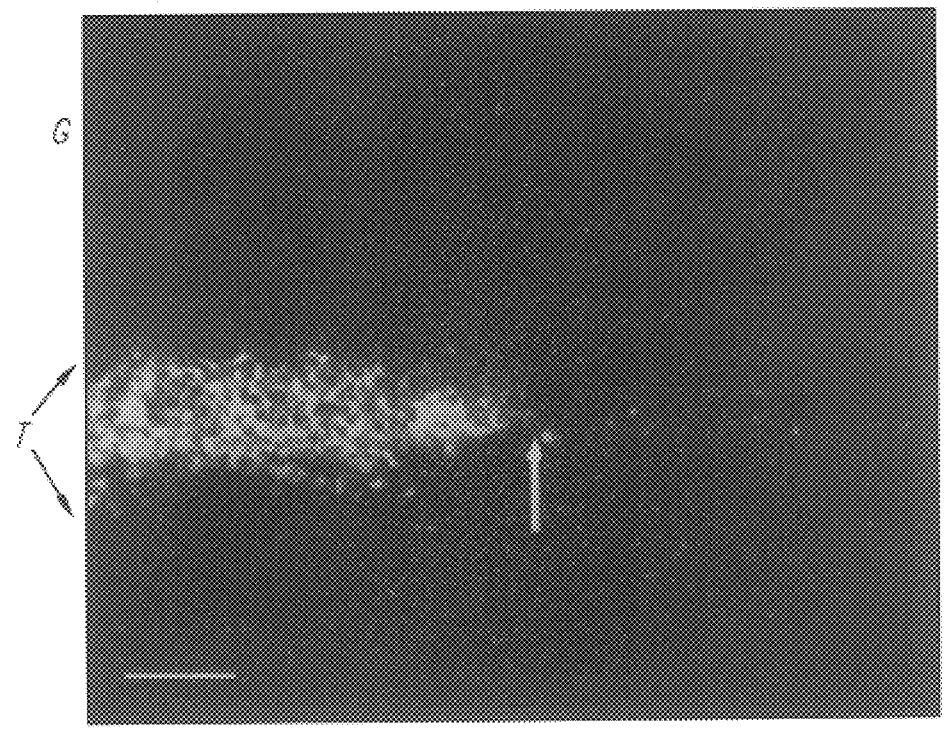
FIG. 25a    FIG. 25b    FIG. 25c
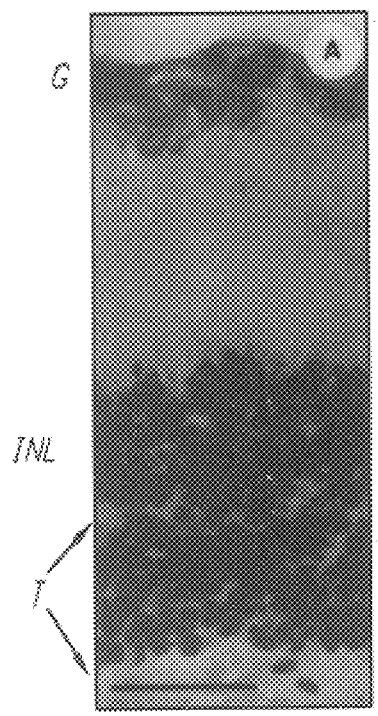 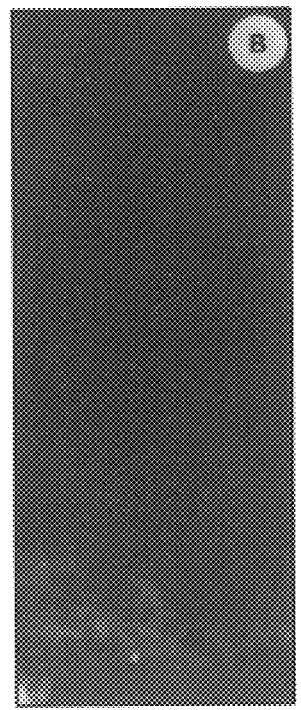 

NORMAL : DARK

NORMAL : STROBE

DYST + TRANS : DARK

DYST + TRANS : STROBE

LIGHT TIME: 0 sec

RECONSTRUCTED RETINA

LIGHT TIME: 5 sec

RECONSTRUCTED RETINA

LIGHT TIME: 0 sec

SHAM

LIGHT TIME: 5 sec

SHAM

RETINAL CELL TRANSPLANT

This application is a continuation of Ser. No. 07/566,996 filed Aug. 13, 1990, abandoned, which is a continuation in part of Ser. No. 07/394,377 filed Aug. 14, 1989, abandoned.

BACKGROUND OF THE INVENTION

The present invention relates in general to surgical instruments, surgical techniques, and cell and tissue isolation techniques. More particularly, the present invention is directed to a surgical tool for transplanting retinal cells, epithelium and choroidea within their normal planar configuration, a graft for transplantation to the subretinal region of the eye, a method for preparing such grafts for transplantation, and a method for reconstructing dystrophic retinas, retinal pigment epithelial layers and choroids.

The retina is the sensory epithelial surface that lines the posterior aspect of the eye, receives the image formed by the lens, transduces this image into neural impulses and conveys this information to the brain by the optic nerve. The retina comprises a number of layers, namely, the ganglion cell layer, inner plexiform layer, inner nuclear layer, outer plexiform layer, outer nuclear layer, photoreceptor inner segments and outer segments. The outer nuclear layer comprises the cell bodies of the photoreceptor cells with the inner and outer segments being extensions of the cell bodies.

The choroid is a vascular membrane containing large branched pigment cells that lies between the retina and the sclerotic coat of the vertebrate eye. Immediately between the choroid and the retina is the retinal pigment epithelium which forms an intimate structural and functional relationship with the photoreceptor cells.

Several forms of blindness are primarily related to the loss of photoreceptor cells caused by defects in the retina, retinal pigment epithelium, choroid or possibly other factors (e.g. intense light, retinal detachment, intraocular bleeding). In several retinal degenerative diseases select populations of cells are lost. Specifically, in macular degeneration and retinitis pigmentosa retinal photoreceptors degenerate while other cells in the retina as well as the retina's central connections are maintained. In an effort to recover what was previously thought to be an irreparably injured retina, researchers have suggested various forms of grafts and transplantation techniques, none of which constitute an effective manner for reconstructing a dystrophic retina.

The transplantation of retinal cells to the eye can be traced to a report by Royo et al., *Growth* 23: 313–336 (1959) in which embryonic retina was transplanted to the anterior chamber of the maternal eye. A variety of cells were reported to survive, including photoreceptors. Subsequently del Cerro was able to repeat and extend these experiments (del Cerro et al., *Invest. Ophthalmol. Vis. Sci.* 26: 1182–1185, 1985). Soon afterward Turner, et al. *Dev. Brain Res.* 26:91–104 (1986) showed that neonatal retinal tissue could be transplanted into retinal wounds.

In related studies, Simmons et al., *Soc. Neurosci. Abstr.* 10: 668 (1984) demonstrated that embryonic retina could be transplanted intracranially, survive, show considerable normal development, be able to innervate central structures, and activate these structures in a light-dependent fashion. Furthermore, these intracranial transplants could elicit light-dependent behavioral responses (pupillary reflex) that were mediated through the host's nervous system. Klassen et al., *Exp. Neurol.* 102: 102–108 (1988) and Klassen et al. *Proc. Natl. Acad., Sci. USA* 84:6958–6960 (1987).

Li and Turner, *Exp. Eye Res.* 47:911 (1988) have proposed the transplantation of retinal pigment epithelium (RPE) into the subretinal space as a therapeutic approach in the RCS dystrophic rat to replace defective mutant RPE cells with their healthy wild-type counterparts. According to their approach, RPE were isolated from 6- to 8-day old black eyed rats and grafted into the subretinal space by using a lesion paradigm which penetrates through the sclera and choroid. A 1 $\mu$l injection of RPE (40,000–60,000 cells) was made at the incision site into the subretinal space by means of a 10 $\mu$l syringe to which was attached a 30 gauge needle. However, this method destroys the cellular polarity and native organization of the donor retinal pigment epithelium which is desirable for transplants.

del Cerro, (del Cerro et al., *Invest. Ophthalmol. Vis. Sci.* 26: 1182–1185, 1985) reported a method for the transplantation of tissue strips into the anterior chamber or into the host retina. The strips were prepared by excising the neural retina from the donor eye. The retina was then cut into suitable tissue strips which were then injected into the appropriate location by means of a 30 gauge needle or micropipette with the width of the strip limited to the inner diameter of the needle (250 micrometers) and the length of the strip being less than 1 millimeter. While del Cerro reports that the intraocular transplantation of retinal strips can survive, he notes that the procedure has some definite limitations. For instance, his techniques do not allow for the replacement of just the missing cells (e.g. photoreceptors) but always include a mixture of retinal cells. Thus, with such a transplant appropriate reconstruction of the dystrophic retina that lacks a specific population of cells (e.g., photoreceptors) is not possible.

del Cerro et al., *Neurosci. Lett.* 92: 21–26, 1988, also reported a procedure for the transplantation of dissociated neuroretinal cells. In this procedure, the donor retina is cut into small pieces, incubated in trypsin for 15 minutes, and triturated ii nto a single cell suspension by aspirating it through a fine pulled pipette. Comparable to the Li and Turner approach discussed above, this procedure destroys the organized native structure of the transplant, including the donor outer nuclear layer; the strict organization of the photoreceptors with the outer segments directed toward the pigment epithelium and the synaptic terminals facing the outer plexiform layer are lost. Furthermore, no means of isolating and purifying any given population of retinal cells (e.g. photoreceptors) from other retinal cells was demonstrated.

It is believed by the present inventor that it is necessary to maintain the photoreceptors in an organized outer nuclear layer structure in order to restore a reasonable degree of vision. This conclusion is based on the well known optical characteristics of photoreceptors (outer segments act as light guides) and clinical evidence showing that folds or similar, even minor disruptions in the retinal geometry can severely degrade visual acuity.

SUMMARY OF THE INVENTION

Among the objects of the present invention, therefore, may be noted the provision of a method for preparation of a graft for use in the reconstruction of a dystrophic retina; the provision of such a method which conserves relatively large expanses of the tissue harvested from a donor eye; the provision of such a method in which the polarity and organization of the cells at the time of harvest are maintained in the graft; the provision of a graft for use in the reconstruction of a dystrophic retina; the provision of such a graft which facilitates regrowth of photoreceptor axons by maintaining the polar organization of the photoreceptor and the close proximity of their postsynaptic targets with the adjacent outer plexiform layer upon transplantation; the provision of a surgical tool for use in the transplantation method which allows appropriate retinotopic positioning and which protects photoreceptors or other grafted tissue from damage prior to and as the surgical device is positioned in the eye; and the provision of a method for transplantation of grafts to the subretinal area of an eye.

Briefly, therefore, the present invention is directed to a method for the preparation of a graft for transplantation to the subretinal area of a host eye. The method comprises providing donor tissue and harvesting from that tissue a population of cells selected from retinal cells, epithelial tissue or choroidal tissue, the population of cells having the same organization and cellular polarity as is present in normal tissue of that type. The population of cells is laminated to a non-toxic and flexible composition which substantially dissolves at body temperature.

The present invention is further directed to a method for the preparation of a graft comprising photoreceptor cell bodies for transplantation to the subretinal area of a host eye. The method comprises providing a donor retina containing a layer of photoreceptor cell bodies. The layer of photoreceptor cell bodies is isolated from at least one other layer of cells of the donor retina in a manner that maintains the layer of photoreceptor cell bodies in the same organization and cellular polarity as is present in normal tissue of that type.

The present invention is further directed to a graft for transplantation to the subretinal area of a host eye. The graft comprises a laminate of a non-toxic and flexible composition which substantially dissolves at body temperature and a population of cells harvested from a donor eye, the population of cells being selected from retinal cells, epithelial tissue and choroidal tissue. The population of cells has the same organization and cellular polarity as is present in normal tissue of that type.

The present invention is further directed to a graft for transplantation to the subretinal area of a host eye. The graft comprises a population of photoreceptor cell bodies harvested from a donor retina, the population of photoreceptor cell bodies having the same organization and cellular polarity as is present in normal tissue of that type, the graft having an essential absence of at least one layer of cells present in the donor retina.

The present invention is further directed to a method for transplanting to the subretinal area of a host's eye a graft comprising a population of cells. The method comprises providing a graft comprising a population of cells selected from retinal cells isolated from at least one other layer of cells within the retina, epithelial tissue and choroidal tissue, the population of cells being maintained in the same organization an t cellular polarity as is present in normal tissue of that type. An incision is made through the host's eye, the retina is at least partially detached to permit access to the subretinal area and the graft is positioned in the accessed subretinal area.

The present invention is further directed to an instrument for the implantation of an intact planar cellular structure between the retina and supporting tissues in an eye. The instrument comprises an elongate supporting platform for holding the planar cellular structure. The platform has a distal end for insertion into an eye, and a proximal end. The distal edge of the platform is convexly curved for facilitating the insertion of the platform into the eye and the advancement of the platform between the retina and the supporting tissues. The instrument has a side rail on each side of the platform for retaining the planar cellular structure on the platform, the distal ends of the side rails being rounded, and the distal portions of the side rails tapering toward the distal end of the platform to facilitate the insertion of the instrument between the retina and the supporting tissue.

The present invention is further directed to an instrument for the implantation of an intact planar cellular structure between the retina and supporting tissues in an eye. The instrument comprises an elongate tube, having a flat, wide cross-section, with a top, a bottom for supporting the planar cellular structure, and opposing sides. The tube has a beveled distal edge facilitating the insertion of the tube into the eye and the advancement of the tube between the retina and the supporting tissues. The instrument also comprises plunger means for ejecting a planar cellular structure from the distal end of the tube.

The present invention is further directed to a kit for transplantation of a graft to the subretinal area of a host eye. The kit contains a graft comprising a population of cells selected from retinal cells, epithelial tissue and choroidal tissue, the population of cells being maintained in the same organization and cellular polarity as is present in normal tissue of that type. The kit additionally contains a surgical instrument comprising an elongate tube, having a flat, wide cross-section, with a top, a bottom for supporting the planar cellular structure, and opposing sides. The tube has a beveled distal edge facilitating the insertion of the tube into the eye and the advancement of the tube between the retina and the supporting tissues. The surgical instrument also comprises plunger means for ejecting a planar cellular structure from the distal end of the tube.

Other objects and features of the invention will be in part apparent and in part pointed out hereinafter.

BRIEF DESCRIPTION OF THE DRAWINGS

FIG. 3 is a schematic of a donor retina;

FIG. 4 is a schematic of a flattened retina;

FIG. 5 is a schematic of a flattened retina mounted to a substrate;

FIG. 6 is a schematic of a sectioned retina mounted to a substrate;

FIG. 7 is a schematic of a laminate comprising a retina section on a supporting, stabilizing substrate;

FIG. 8 is a schematic top plan view of the laminate of FIG. 7, showing a graft (dashed lines) comprising a photoreceptor cell layer and a supporting, stabilizing substrate;

FIG. 10 is a side elevation view of a second embodiment of an instrument adapted for implanting an intact planar cellular structure between the retina and supporting tissues in an eye, with the plunger in its retracted position, and with portions broken away to show detail;

FIG. 11 is a top plan view of the instrument shown in FIG. 10;

FIG. 12 is a side elevation view of the instrument of the second embodiment, with the plunger in its extended position, and with portions broken away to show detail;

FIG. 13 is a top plan view of the instrument shown in FIG. 12;

FIG. 24 is a photograph illustrating FITC fluorescent micrograph of antibody Ret P-1 specific for opsin as set forth in Example 1;

FIG. 25 is a series of photograph panels illustrating in A, transplanted photoreceptors attached to recipient or host retina, in B, fluorescent micrograph showing transplanted cells showing DiI fluorescence, identifying them as transplanted tissue, and in C, a micrograph illustrating FITC fluorescence of antibody specific for opsin as set forth in Example 1;

DETAILED DESCRIPTION

As used herein, the term "donor" shall mean the same or different organism relative to the host and the term "donor tissue" shall mean tissue harvested from the same or different organism relative to the host.

Several forms of blindness such as retinitis pigmentosa, retinal detachment, macular degeneration, and light exposure-related blindness, are primarily related to the loss of the photoreceptors in the eye. However, destruction of the photoreceptors does not necessarily lead to the loss of the remaining retina or axons that connect the retina to the brain. Surprisingly, it has been discovered that some degree of vision can be restored by replacing damaged photoreceptors with photoreceptors harvested from a donor and which are maintained in their original organization and cellular polarity.

Figure 1:
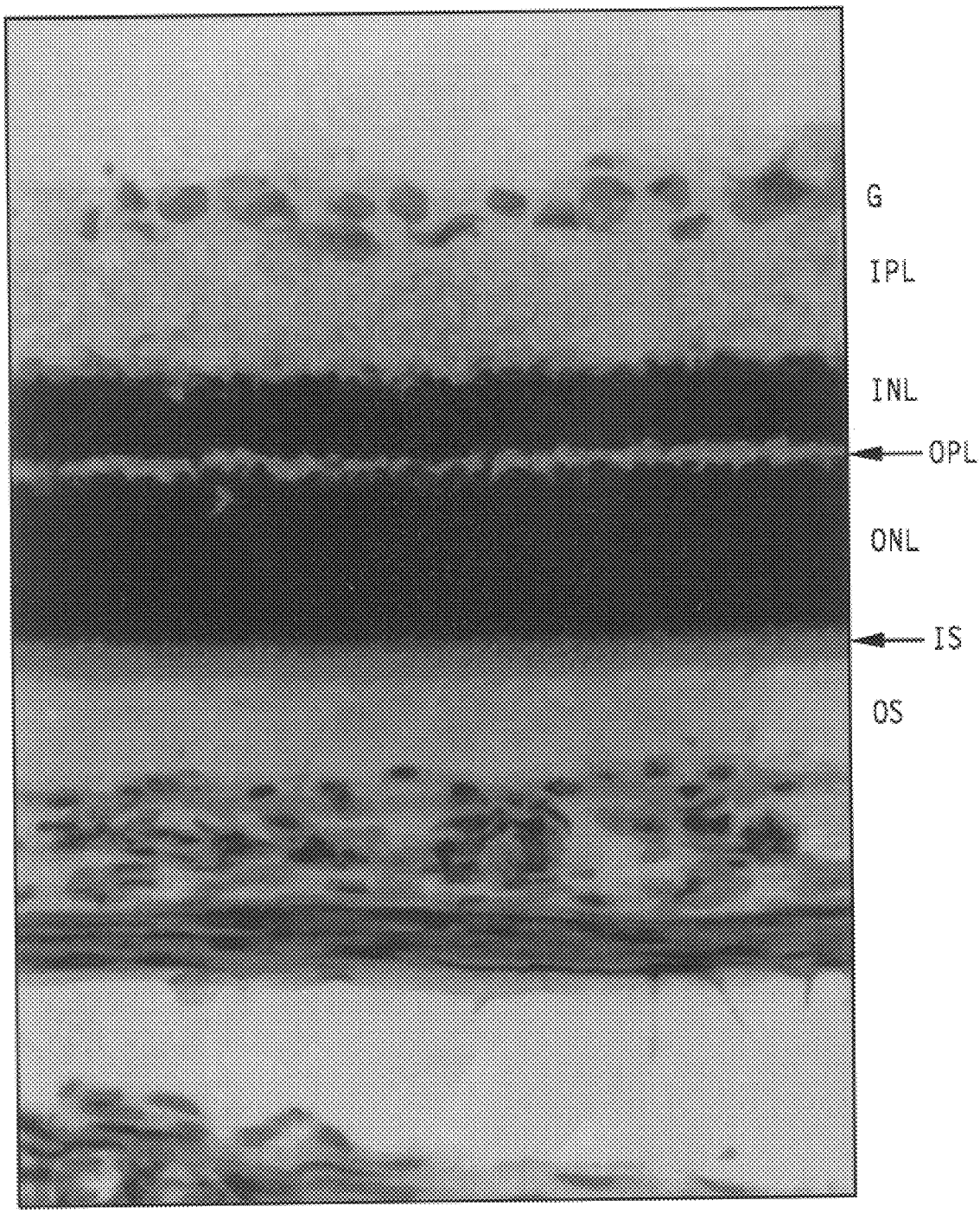
FIG. 1 is a photograph of a cryostat section of normal rat retina as set forth in Example 1.
Figure 2:
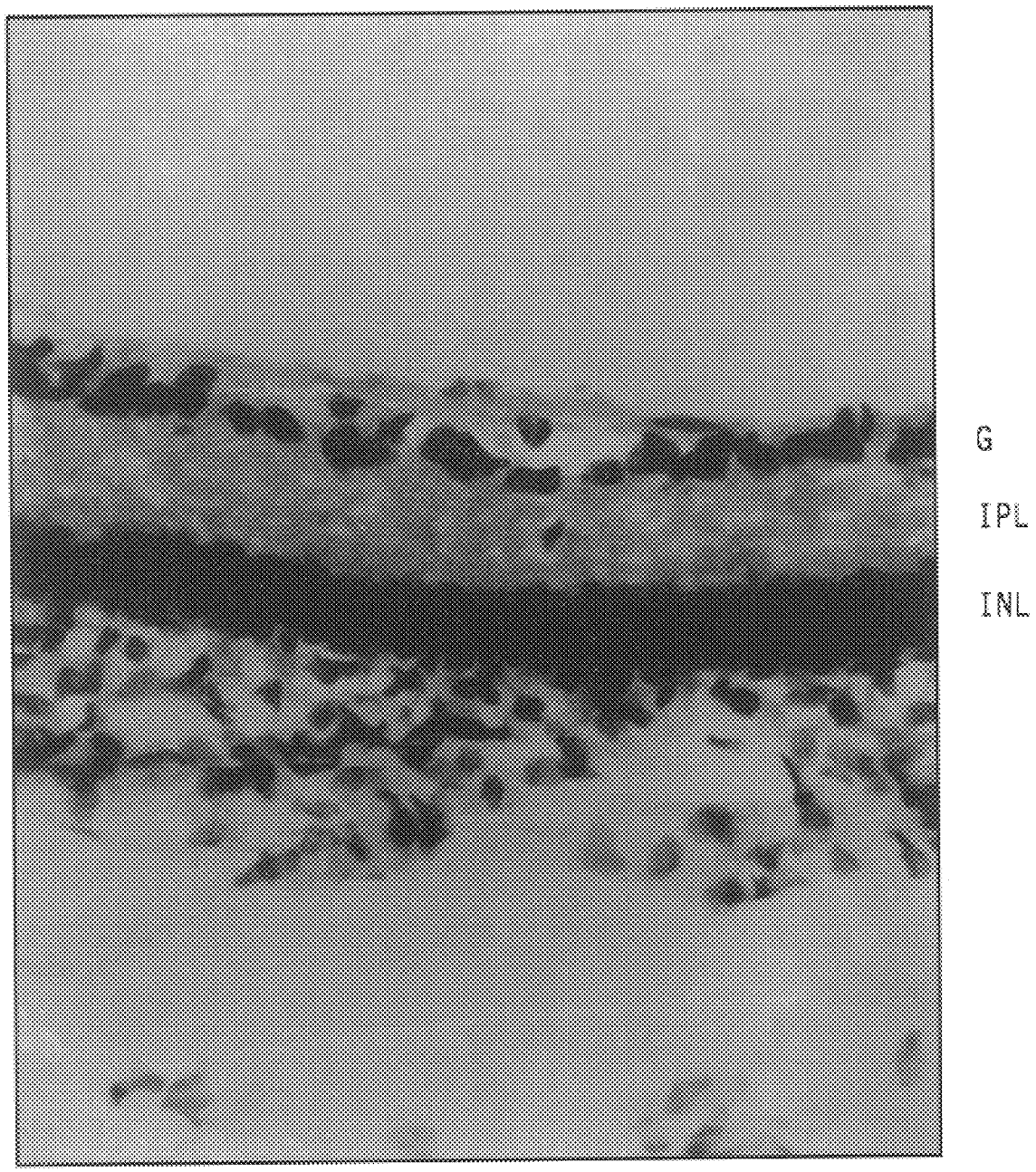
FIG. 2 is a photograph of a blinded rat retina following constant illumination as set forth in Example 1.
Figure 14:
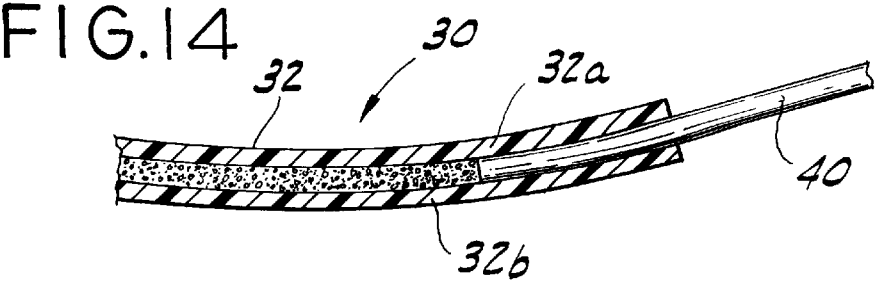
FIG. 14 is a partial longitudinal cross-sectional view of the instrument, showing part of a planar cellular structure loaded therein.

FIG. 1 is a photograph of a cryostat section of normal rat retina. FIG. 2 is a photograph of a cryostat section of a rat retina following constant illumination which destroys the photoreceptor (outer nuclear) layer while leaving other retinal layers and cells largely intact. In these and subsequent figures, the retina or layers thereof, e.g., the ganglion cell layer ("G"), inner plexiform layer ("IPL"), inner nuclear layer ("INL"), outer plexiform layer ("OPL"), outer nuclear layer ("ONL"), inner segments ("IS"), outer segments ("OS"), and retinal pigment epithelium ("RPE"), are shown, respectively, from top to bottom.

Referring now to FIG. 3, a graft comprising photoreceptor cells is prepared in accordance with a method of the present invention by removing a donor retina 50 comprising inner retina layers 52 and photoreceptor layer 54 from a donor eye. The donor retina 50 is flattened (FIG. 4) by making a plurality of cuts through the retina from locations near the center of the retina to the outer edges thereof (see FIG. 8). Cuts can be made in other directions if necessary.

As shown in FIG. 5, the flattened retina 56 is placed with the photoreceptor side 54 down on a gelatin slab 58 which has been surfaced so as to provide a flat surface 60 that is parallel to the blade of a vibratome apparatus. The gelatin slab 58 is secured to a conventional vibratome chuck of the vibratome apparatus. Molten four to five per cent gelatin solution is deposited adjacent the flattened retina/gelatin surface interface 61 and is drawn by capillary action under the flattened retina causing the flattened retina to float upon the gelatin slab 58. Excess molten gelatin is promptly removed and the floating flattened retina is then cooled to approximately 4° C. with ice-cold Ringer's solution that surrounds the gelatin block to cause the molten gelatin to gel and hereby coat the bottom surface of the flattened retina and adhere it to the gelatin block.

As shown in FIG. 6, the inner retina portion 52 is sectioned from the top down at approximately 20 to 50 millimicrons until the photoreceptor layer 54 is reached, thereby isolating the photoreceptor layer from the inner layers of the retina, i.e., the ganglion cell layer, inner plexiform layer, inner nuclear layer, and outer plexiform layer. When the photoreceptor layer is reached, the vibratome stage is advanced and a section from approximately 200 to 300 millimicrons thick obtained as shown in FIG. 7. The thickness of this section is sufficient to undercut the photoreceptor and form a laminate 62 consisting of a layer of photoreceptor cells and the gelatin adhered thereto.

As shown in FIG. 8, the laminate 62 is cut vertically along the dashed lines to create a graft 63 having a size appropriate for transplantation. The surface of the graft should have a surface area greater than about 1 square millimeter, preferably greater than 2 square millimeters, and most preferably greater than 4 square millimeters or as large as may be practically handled. Thus constructed, the graft may subtend a considerable extent of the retinal surface.

The gelatin substrate adds mechanical strength and stability to the easily damaged photoreceptor layer. As a result, the flattened retinal tissue is less likely to be damaged and is more easily manipulated during the transplantation procedure.

Gelatin is presently preferred as a substrate because of its flexibility, apparent lack of toxicity to neural tissue and ability to dissolve at body temperature.

However, other compositions such as ager or agarose which also have the desirable characteristics of gelatin may be substituted. Significantly, gelatin has not been found to interfere with tissue growth or post-transplant interaction between the graft and the underlying retinal pigment epithelium.

Gelatin is presently preferred as an adhesive to laminate the retinal tissue to the substrate. However, other compositions, including lectins such as concanavalin A, wheat germ agglutin, or photoreactive reagents which gel or solidify upon exposure to light and which also have the desirable characteristics of gelatin may be substituted.

Advantageously, the gelatin or other substrate may additionally serve as a carrier for any of a number of trophic factors such as fibroblast growth factor, pharmacologic agents including immunosuppressants such as cyclosporin A, anti-inflamation agents such as dexamethasone, anti-angiogenic factors, anti-glial agents, and anti-mitotic factors. Upon dissolution of the substrate, the factor or agent becomes available to impart the desired effect upon the surrounding tissue. The dosage can be determined by established experimental techniques. The substrate may contain biodegradable polymers to act as slow release agents for pharmacologic substances that may be included in the substrate.

The thickness of the graft comprising the sectioned flattened retinal tissue and the substrate as discussed above is only approximate and will vary as donor material varies. In addition, sectioning may be facilitated and vibratome thickness further calibrated from histological measurements of the thickness of the retina, thereby providing further guides to sectioning depth. Appropriate sectioning thicknesses or depth may be further determined by microscopic examination and observation of the sections.

As an alternative to mechanical, e.g., microtome, sectioning, the donor retina may be chemically sectioned. Specifically it is known that neurotoxic agents such as kainic acid are toxic to cells in all retinal layers except the photoreceptor layer (i.e., kainic acid does not damage photoreceptor cells). Therefore, if the donor retina is treated with an appropriate neurotoxic agent, the photoreceptor layer can be isolated. This technique has the advantage of maintaining the retinal MUller cells (which are not killed by kainic treatment) with the photoreceptor cells. Since it is known that MUller cells help maintain photoreceptor cells (both biochemically and structurally), the isolation of MUller cells along with the photoreceptor cells could be advantageous.

If desired, the graft may additionally contain the retinal pigment epithelial cells. Because the RPE is tenuously adherent to the retina, mechanical detachment of the retina from a donor eye ordinarily will cause the RPE to separate from the retina and remain attached to the choroid. However, through the use of enzymatic techniques such as those described in Mayerson et al., *Invest. Opthalmol. Vis, Sci.* 25: 1599–1609, 1985, the retina can be separated from the donor eye with the RPE attached. In accordance with the present invention, grafts comprising the choroid may additionally be prepared. To do so, the choroid is stripped off of the scleral lining of the eye (with or without the RPE attached), and flattened by making radial cuts. The donor choroid may then be adhered to a substrate as previously described for the photoreceptor cells and/or combined with a photoreceptor layer which has been prepared as described above to form a laminate comprising a photoreceptor layer adhered to a substrate, a RPE layer and a choroidal layer.

Referring again to the Figures there is shown preferred embodiments for the surgical instruments of this invention. The surgical instruments are described in connection with a photoreceptor isolation and transplantation method. The surgical instruments and methods of this invention are particularly adapted for isolation and transplantation of an intact sheet of cells from a donor retina to a recipient retina and are characterized by the maintenance of cell organization of the transplanted tissue layer.

Figure 9:
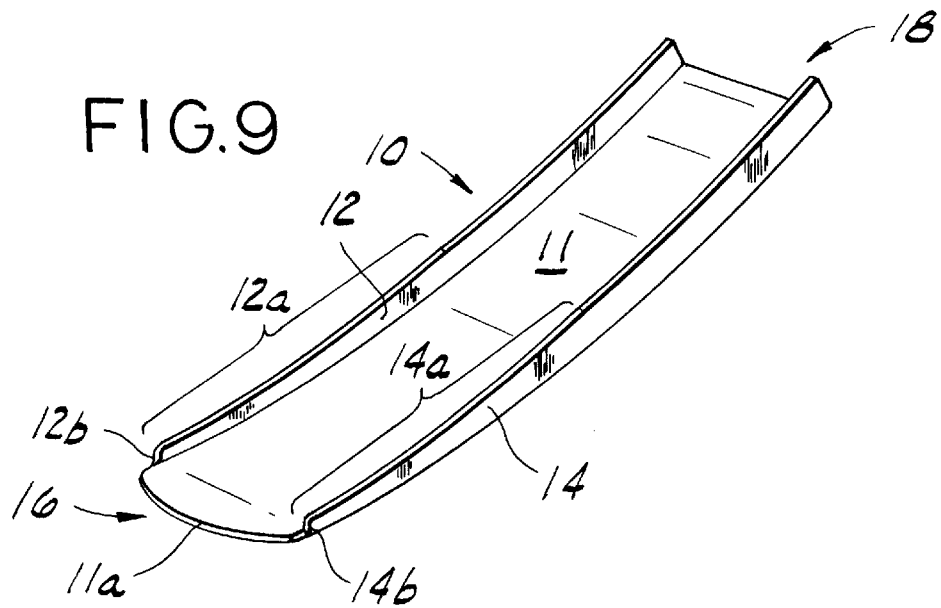
FIG. 9 is a perspective view of a first embodiment of an instrument adapted for implanting an intact planar cellular structure between the retina and supporting tissues in an eye.

A first embodiment of an instrument for implanting an intact planar cellular structure between the retina and supporting tissues in an eye is indicated generally as 10 in FIG. 9. The instrument 10 may be made from acrylic, or some other suitable material that is flexible and sterilizable. The instrument 10 comprises an elongate platform 11 for holding the planar cellular structure. The platform 11 has a distal end 16 for insertion into the eye of the recipient, and a proximal end 18. As shown and described herein the platform 11 is approximately 2 to 10 centimeters long, which is an appropriate length for making implants in rodents and lower primates. The platform 11 must be sufficiently long to extend into the eye, between the retina and the supporting tissue, and thus different platform lengths may be used, depending upon the procedure being employed and upon the recipient. As shown and described herein the platform is approximately 2.5 millimeters wide, which is sufficiently wide for making implants in rodents and lower primates. The platform 11 must be sufficiently wide to carry and intact cellular structure for implanting, and thus different platform widths may be used, depending upon the recipient.

As shown in FIG. 9, the edge 11a of the platform 11 at the distal end 16 is preferably convexly curved to facilitate both the insertion of the instrument 10 into the eye, and the advancement of the instrument between the retina and the supporting tissue to temporarily detach the retina, with a minimum of trauma. The platform 11 is preferably concavely curved (with respect to the top surface of the platform 11) along its longitudinal axis from the distal end 16 to the proximal end 18. The curvature of the platform 11 facilitates the manipulation of the instrument 10 within the eye, particularly the manipulation of the instrument between the retina and the supporting tissue on the curved walls of the eye. The radius of the curvature of the platform 11 will depend upon the procedure and the recipient.

The platform 11 has side rails 12 and 14 on opposite sides for retaining the planar cellular structure on the platform. As shown in FIG. 9, the distal portions 12a and 14a of the side rails taper from a point intermediate the distal and proximal ends of the side rails toward their distal ends. The distal ends of the side rails terminate in smoothly curved ends 12b and 14b, which are proximal of the distal end 16 of the platform. The offset of the distal ends of the rails, together with their rounded configuration facilitates the insertion of the instrument into the eye and the advancement of the instrument between the retina and the supporting tissue. As shown and described herein, the proximal portions of the side rails 12 and 14 are approximately 1 millimeter high, while the distal portions 12a and 14a taper to about 0.5 millimeters. The height of the side rails is made as small as possible, but they must be slightly greater than the thickness of the planar cell structure and the supporting substrate, and thus may vary depending on the donor and the type of implantation being made (ie, how many cell layers are being implanted and thickness of the substrate).

A second embodiment of an instrument for implanting an intact planar cellular structure between the retina and supporting tissues in an eye is indicated generally as 30 in FIGS. 10–14, and 18. The instrument 30 may be made from polyethylene, or some other suitable material that is flexible and sterilizable. For example, the instrument might be made of silicone rubber or silastic. The instrument 30 comprises an elongate tube 32 having a flat, wide cross-section, with a top 32a, a bottom 32b for supporting the planar cellular structure, and opposing sides 32c and 32d. The tube 32 has a distal end 34 for insertion into the eye, and a proximal end 36. The distal end 34 of the tube 32 is open for the discharge of the planar cellular structure. The instrument 30 of the second embodiment is preferable to the instrument 10 of the first embodiment in at least one respect because the tube 32 has a top 32a which provides better protection for the planar cellular structure to be implanted than the open platform 11.

As shown and described herein the tube 32 is approximately 3.5 centimeters long, which is an appropriate length for making implants in rodents and lower primates. The tube 32 must be sufficiently long to extend into the eye, between the retina and the supporting tissue, and thus the different tube lengths may be used, depending upon the procedure being employed and upon the recipient. As shown and described herein the tube is approximately 2.5 centimeters wide, which is sufficiently wide for making implants in rodents and lower primates. The tube must be sufficiently wide to carry an intact cellular structure for implanting, and thus different tube widths may be used, depending upon the recipient. As shown and described herein, the sides 32c and 32d are approximately 0.75 millimeters high. The height of the sides is made as small as possible, but they must be slightly greater than the thickness of the planar cell structure and substrate, and thus may vary depending on the donor and the type of implantation being made (i.e. how many cell layers are being implanted and thickness of the substrate).

The distal end 34 of the tube can be beveled to facilitate both the insertion of the tube into the eye, and the advancement of the tube between the retina and the supporting tissues, with a minimum of trauma. The end is preferably beveled at about 45°, from the top 32a to the bottom 32b. As shown in FIGS. 10 and 12, the distal end 34 of the tube 32 is also preferably raked transversely across the tube (i.e. from side 32c to 32d) toward the proximal end. The rake angle is preferably about 45°. The raked distal end also facilitates the insertion of the tube into the eye, and the advancement of the tube between the retina and the supporting tissue. Moreover, raking the distal end eliminates a sharp corner that could damage tissue.

The tube 32 is preferably concavely curved along its longitudinal axis from the distal end 34 to the proximal end 36, so that the top 32a is on the inside of the curve, and the bottom 32b is on the outside of the curve. The curvature of the tube facilitates the manipulation of the instrument 30 within the eye, particularly the manipulation of the instrument between the retina and the supporting tissue on the curved walls of the eye. The radius of the curvature of the tube will depend on the procedure and on the recipient.

The instrument 30 also comprises plunger means. As shown in FIGS. 10–14, the plunger means is preferably a flat plunger 40 slidably received in the tube so that relative sliding motion between the tube 32 and the plunger 40 urges a planar cellular structure that is in the tube out the distal end of the tube. The plunger 40 may be made of polymethylmethacrylate. The proximal end of the plunger 40 projects a sufficient amount from the proximal end of the tube 32 that the end of the plunger can be manipulated even when the distal portion of the tube is in an eye. The preferred method of operating the instrument 30 is that once the distal end of the tube is properly located within the subretinal area, the plunger 40 is held in place as the tube 32 is gradually withdrawn to eject the cellular structure.

Figure 18:
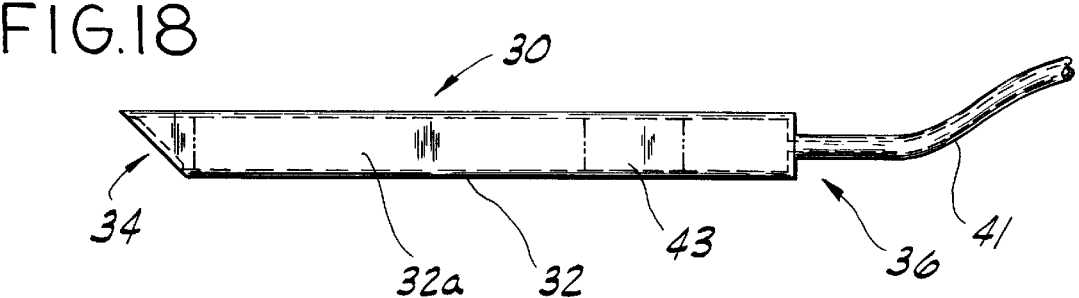
FIG. 18 is a top plan view of the second embodiment, showing an alternative plunger means.

Alternatively, as shown in FIG. 18, the plunger means may comprise means for applying hydraulic pressure on the contents of the tube. In this case the proximal end 36 of the tube 32 is connected to a line 41 connected to a source of fluid under pressure. Fluid can be selectively supplied via the line 41 to the proximal end of the tube, to displace the contents of the tube. The fluid may be viscous, for example a 2% carboxymethylcellulose, or non-viscous. Particularly in the later case, it may be desirable to have a block 43 of gelatin or some other substance in the tube to act as a mechanical plunger and to separate the fluid from the cell structure being implanted. Gelatin is satisfactory because it is a semi-solid, and because it will dissolve harmlessly if it is ejected from the tube.

As shown in FIGS. 10–13, the instrument 30 preferably also includes a lumen 42, extending generally parallel with the tube 32. As used herein, lumen refers to any tube-like vessel, whether separately provided or formed as a passageway in another structure. The lumen 42 is attached to one of the sides of the tube 32, and preferably side 32c so that the distal end of the tube rakes away from the lumen. The lumen 42 has a distal end 44 generally adjacent the distal end of the tube, and preferably slightly advanced relative to the distal end of the tube. The proximal end 46 is remote from the distal end, and may be provided with a connector 48 for connection with a source of fluid under pressure. Thus the lumen 42 can eject a stream of fluid from its distal end 44 which creates a fluid space ahead of the instrument, which helps separate or detach the retina from the supporting tissue as the instrument is advanced. The fluid may be a saline solution, or some other fluid that will not harm the delicate eye tissues. Various substances, such as anti-oxidants, anti-inflammatories, anti-mitotic agents and local anesthetics can be provided in the fluid for treatment of the eye or implanted tissue.

The raked distal end of the tube 32 follows generally in the path opened by the fluid, thus minimizing direct contact of the instrument and the eye tissue. The distal end of the lumen may be beveled to facilitate the advancement of the instrument, particularly at times when fluid is not being ejected from the lumen. The end is preferably beveled at about 45°. Of course, rather than provide a separate lumen 42, the lumen could be formed integrally in the walls of the tube 32.

Figure 15:
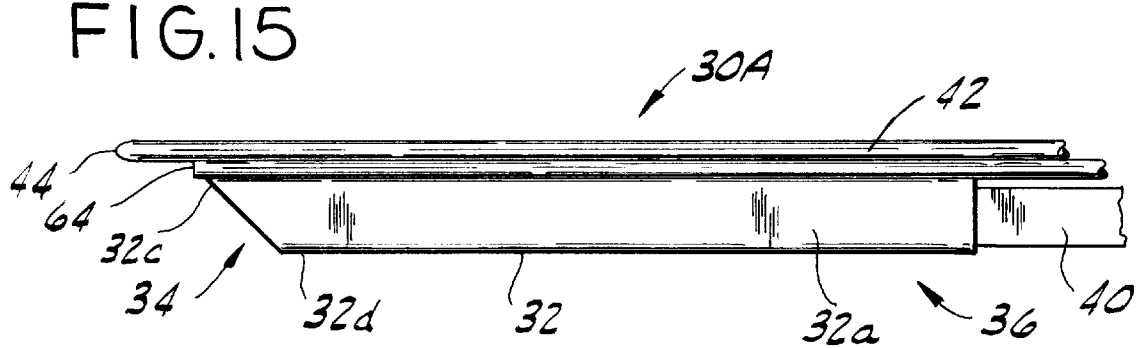
FIG. 15 is a top plan view of a first alternative construction of the second embodiment.

A first alternate construction of instrument 30 is indicated as 30A in FIG. 15. The instrument 30A is very similar in construction to instrument 30, and corresponding parts are identified with corresponding reference numerals. However, unlike instrument 30, the instrument 30A includes a fiber optic filament 64 extending generally parallel with lumen 42, and positioned between the lumen 42 and the tube 32. The fiber optic filament 64 facilitates the manipulation of the instrument and the proper placement of the implant in two ways: a light source can be provided at the proximal end of the fiber optic filament so that the filament provides light at the distal end of the instrument, to facilitate the visual observation procedure through the pupil. Alternatively, a lens could be provided at the proximal end of the fiber optic filament so that the filament can also be used for direct observation at the distal end of the instrument.

Additionally, the fiber optic filament could allow for laser-light cautery to control subretinal bleeding. Of course, rather than provide a separate fiber optic filament 64, fiber optic filaments could be incorporated into the walls of the tube 32 or the lumen 42.

Figure 16:
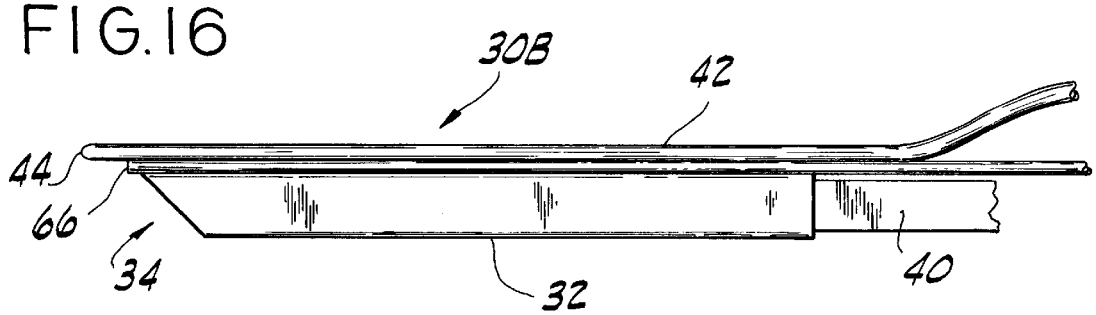
FIG. 16 is a top plan view of a second alternative construction of the second embodiment.

A second alternative construction of instrument 30 is indicated as 30B in FIG. 16. The instrument 30B is very similar in construction to instrument 30, and corresponding parts are identified with corresponding reference numerals. However, unlike instrument 30, the instrument 30B includes a lumen 66 extending generally parallel with lumen 42, and positioned between the lumen 42 and the tube 32. The lumen 66 allows for the aspiration of material from the distal end of the instrument. The proximal end of the lumen 66 can be connected to a source of suction, to remove excess fluid and debris. It is possible to incorporate the lumen 66 into the wall of the tube 32.

Figure 17:
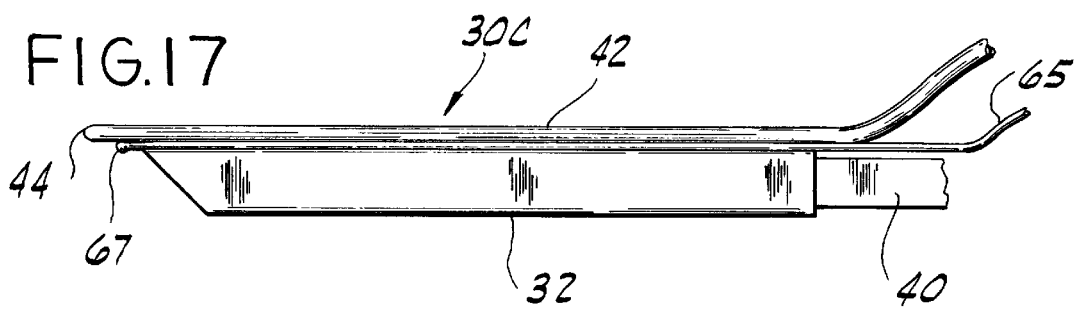
FIG. 17 is a top plan view of a third alternative construction of the second embodiment.

A third alternative construction of the instrument 30 is indicated as 30C in FIG. 17. The instrument 30C is very similar in construction to instrument 30, and corresponding parts are identified with corresponding reference numerals. However, unlike instrument 30, the instrument 30C includes a pair of lead wires 65, terminating in an electrode 67 at their distal ends. The electrode 67 allows for cauterization of blood vessels. The proximal ends of the leads 65 can be connected to a source of electrical power to seal broken blood vessels. It is possible to incorporate the leads 65 into the wall of the tube 32.

Of course, two or more of the features described with respect to the alternate embodiments 30A, 30B, and 30C could be combined, if desired.

Figure 19:
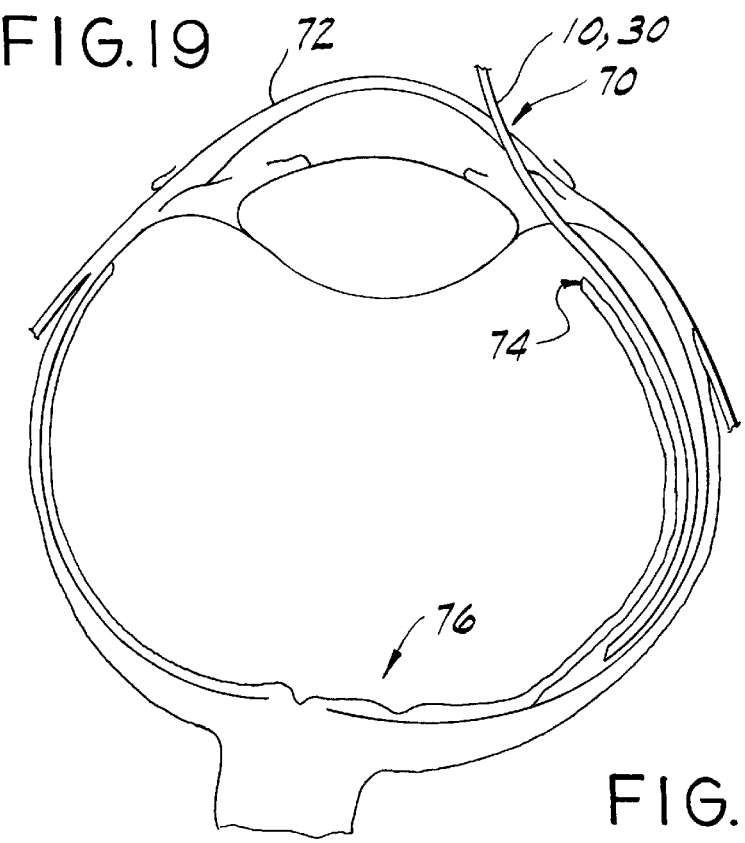
FIG. 19 is a horizontal section through an eye illustrating a trans-corneal surgical approach.

To transplant the retinal cells, including photoreceptors, the host eye is prepared so as to reduce bleeding and surgical trauma. A transcorneal surgical approach to the subretinal space is one such approach and it will be understood that other surgical approaches, such as transscleral and choroidal may also be used. The preferred surgical approach in the rodent, FIG. 19, includes making a transverse incision 70 in a cornea 72 of sufficient size so as to allow insertion of a surgical instrument illustrated schematically by reference characters 10 or 30. The instrument 10 is advanced under the iris, through the cornea 72 and to the ora serrata 74 as illustrated in FIG. 19. The iris should be dilated for example, with topical atropine. When the instrument 10 is used, it detaches the retina as it is advanced under the retina and into the sub-retinal space to the posterior pole 76 of the eye.

The channel defined by the side rails 12, 14 and the intermediate cell supporting platform provides for the graft comprising a photoreceptor layer 54 attached to the gelatin substrate to be placed on the instrument 10 and guided into the sub-retinal space, preferably with forceps or other suitable instruments. After positioning the photoreceptor layer at the desired transplant site, the gelatin is held in position with the forceps while the carrier is removed. The edges of the corneal incision are abutted after removal of the forceps to allow rapid, sutureless healing. The eye should be patched during recovery.

If the surgical instrument 30 (FIGS. 10–14, and 18) is used instead of the instrument 10, the graft comprising intact generally planar sheet 54 of donor photoreceptors attached to the gelatin substrate 62 is drawn into the elongate tube 32. The instrument 30 is then inserted through an appropriate sized incision in the cornea and advanced under the iris. The iris will have been dilated, for example, with topical atropine. The instrument 30 is advanced to the ora serrata 74 of the host eye. If the instrument 30 includes a lumen 42, the retina is detached by the gentle force of a perfusate such as a saline-like fluid, carboxymethylcellulose, or 1–2% hyluronic acid ejected from the lumen 42. Advantageously, the fluid may additionally contain anti-oxidants, anti-inflammation agents, anesthetics or agents that slow the metabolic demand of the host retina.

If the instrument 30 does not include a lumen 42, the retina is detached by the walls of the surgical instrument as it is advanced under the retina and into the subretinal space to the posterior pole 76 of the eye. The graft comprising a photoreceptor layer attached to the gelatin substrate is then transplanted by moving the tube 32 in a direction away from the eye while keeping the plunger 40 stationary. The plunger 40 is carefully withdrawn out of the eye and the edges of the corneal incision are abutted after removal to allow rapid, sutureless healing. Retinal reattachment occurs rapidly and the photoreceptor sheet is held in place in a sandwich-like arrangement between the retina and the underlying eye tissues. The incision may require suturing.

Figure 20:
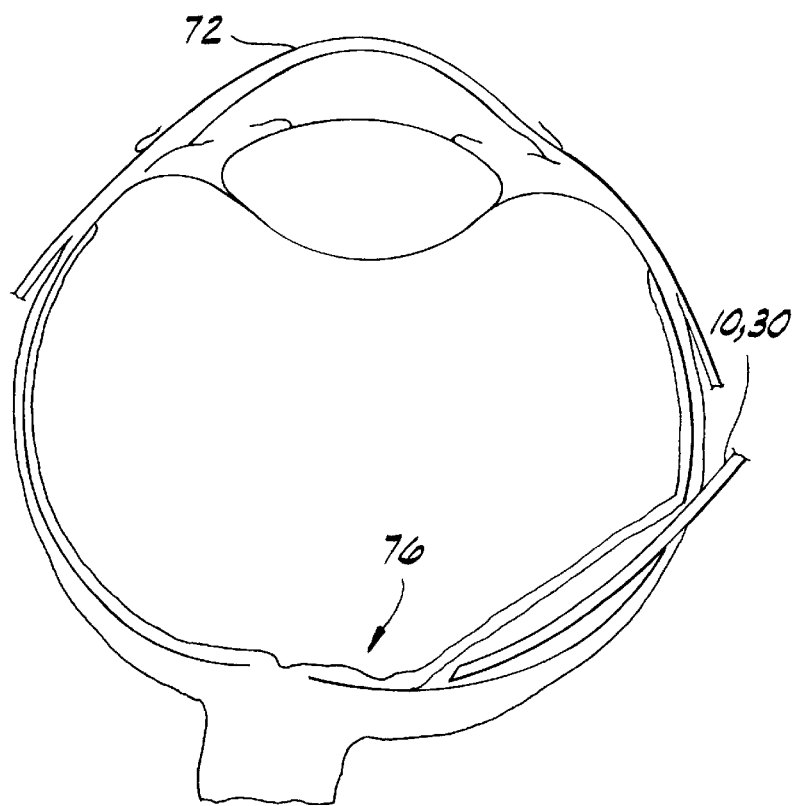
FIG. 20 is a horizontal section through an eye illustrating a trans-choroidal and scleral surgical approach.
Figure 21:
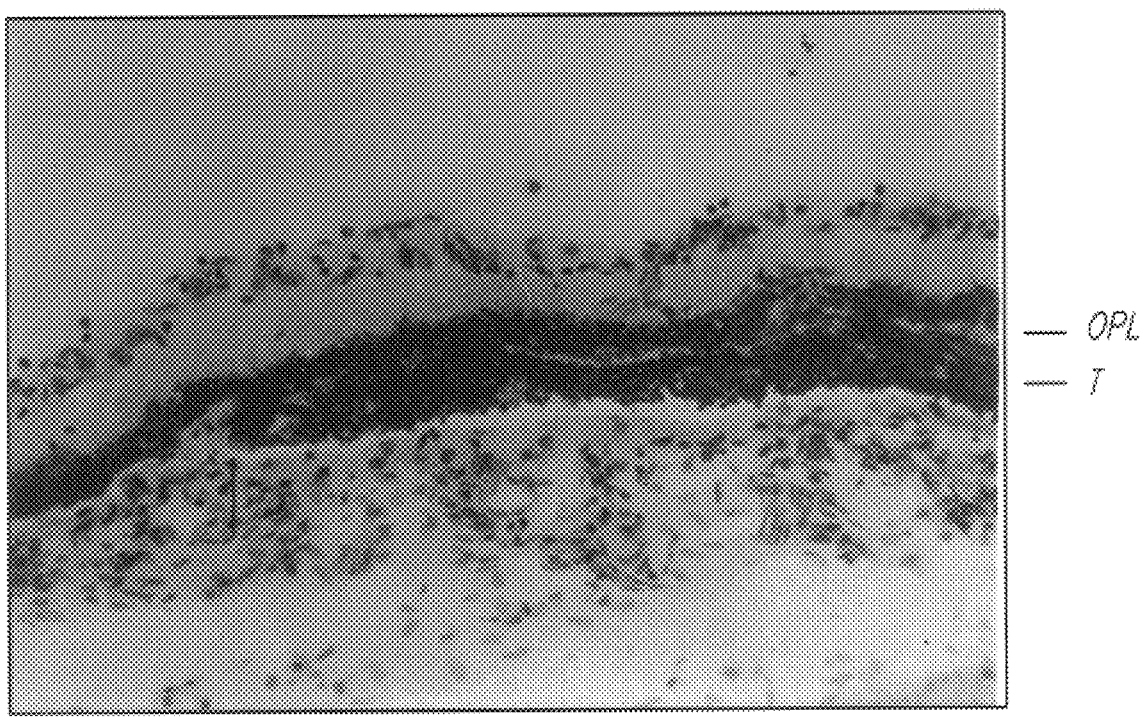
FIG. 21 is a photograph of transplanted photoreceptors as set forth in Example 1.

FIG. 20 depicts a trans-choroidal and scleral surgical approach as an alternative to the transcorneal approached described above. Except for the point of entry, the surgical technique is essentially the same as outlined above. Nevertheless, the transcorneal approach is preferred because it has been found to reduce bleeding and surgical trauma.

A further surgical approach is to diathermize in the pars plana region to eliminate bleeding. The sclera is then incised and the choroidal and epithelial tissue is diathermized. The surgical tool is then inserted through the incision, the retina is intercepted at the ora serrata and the graft is deposited in the subretinal area otherwise as outlined elsewhere herein.

In yet a further surgical approach, entry is gained through the pars plana area as outlined above and an incision is made in the retina adjacent to the retinal macula. The surgical tool is then inserted through the retinotomy and into the macular area.

It is known that the retina does not necessarily undergo glial scar formation when it is damaged, unlike the adult central nervous system as disclosed by Bigami et al., *Exp. Eye Res.* 28:63–69, (1979), and McConnel et al., *Brain Res.* 241:362–365 (1982). McConnel et al. suggest that this characteristic lack of scar tissue contribute to a potential of retinal cells to regrow severed axons within the eye.

In accordance with the present invention, it has recognized that regrowth of photoreceptor axons may be facilitated by the proximity of the post-synaptic targets of the photoreceptor within the adjacent outer plexiform layer. In addition, growth across substantial intervening neural or glial scar tissue is not necessary in order for transplanted photoreceptors to make appropriate connections with the recipient retina including neural connections.

The following examples illustrates the invention.

EXAMPLE 1

Experimental Animals

Adult albino rats (Sprague-Dawley) were exposed to constant illumination averaging 1900 lux for 2 to 4 weeks as described in O'Steen, *Exp. Neurol.* 27:194 (1970).

As shown in FIG. 1, this exposure destroys most photoreceptors, eliminating cells of the outer nuclear layer but leaving the remaining neural retina intact. Photoreceptors for transplantation were taken from 8-day-old normal rats of the same strain that had been maintained under colony room illumination (10–20 lux) on a 12 hr/12 hr light/dark cycle. Experimental animals were anesthesized with ketamine and sodium pentobarbital. A preoperative dose of dexamethasone (10 mg/kg IP) was also administered.

Photoreceptor Preparation

The retina from the anesthetized 8-day-old rat was removed, flattened with radial cuts and placed with the receptor side down on a gelatin slab secured to the vibratome chuck. Molten gelatin (4–5% solution) was deposited adjacent the retina at the retina/gelatin interface and then cooled to 4° C. with ice-cold Ringer's solution. The retina was sectioned at 20 to 50µm until the photoreceptor layer was reached. When the photoreceptor layer was reached, the stage was advanced and a thick (200 to 300 µm) section was taken, undercutting the photoreceptor layer secured to the gelatin base.

DiI Labeling

The isolated outer nuclear layer was cultured overnight with 40 μg/ml of diI (1,1'-dioctadecyl-3,3,3',3'-tetramethylindocarbocyanine perchlorate in Earle's MEM containing 10% fetal calf serum, incubated under 95%/5% oxygen/carbon dioxide mixture at room temperature. Labeling techniques and fluorescent microscopy were otherwise as outlined by Honig et al., *J. Cell. Biol.* 103:17, 1986. DiI was removed from sections that were to be counterstained with FITC-labeled RET-P1 opsin antibody by prior washing in acetone.

Surgical Procedure

A transverse incision was made in the cornea sufficient to allow insertion of a surgical instrument 10 that is 2.5 mm wide with side rails 0.5 mm high or surgical instrument 30. The instrument was advanced under the iris (dilated with topical atropine) to the ora serrata, detaching the retina. The carrier was then advanced under the retina into the subretinal space to the posterior pole of the eye. The instrument allowed a graft comprising a piece of the photoreceptor layer attached to the gelatin substrate (up to 2.5×4 mm) to be guided into the retinal space by fine forceps. The instrument was then removed while the gelatin was held in position by the forceps. Following removal of the forceps, the edges of the corneal incision were abutted to allow rapid, sutureless healing. The eye was patched during recovery and a prophylactic dose of penicillin was administered. Upon removal of the patch, a verterinary ophthalmic antibiotic ointment was applied.

Transplant recipients were maintained on a 12 hr/12 hr light/dark cycle with an average light intensity of 50 lux. Following appropriate survival times, the animal was overdosed with pentobarbital and perfused transcardially with phosphate buffered 3% paraformaldehyde-2% gluteraldehyde solution. Cryostat sections of both the light-blinded eye (control) and the eye receiving the photoreceptor transplant were then cut (20 μm).

Immunohistochemistry

Antibody labeling for opsin was performed on retinas fixed with 3% paraformaldehyde and cryosectioned at 20 μm. Immunohistocheinical methods were otherwise as described in Hicks, et al., *J. Histochem Cytochem* 35:1317 (1987). Elimination of the primary antibody eliminated specific labeling for opsin.

Cryostat Sections

Figure 22:
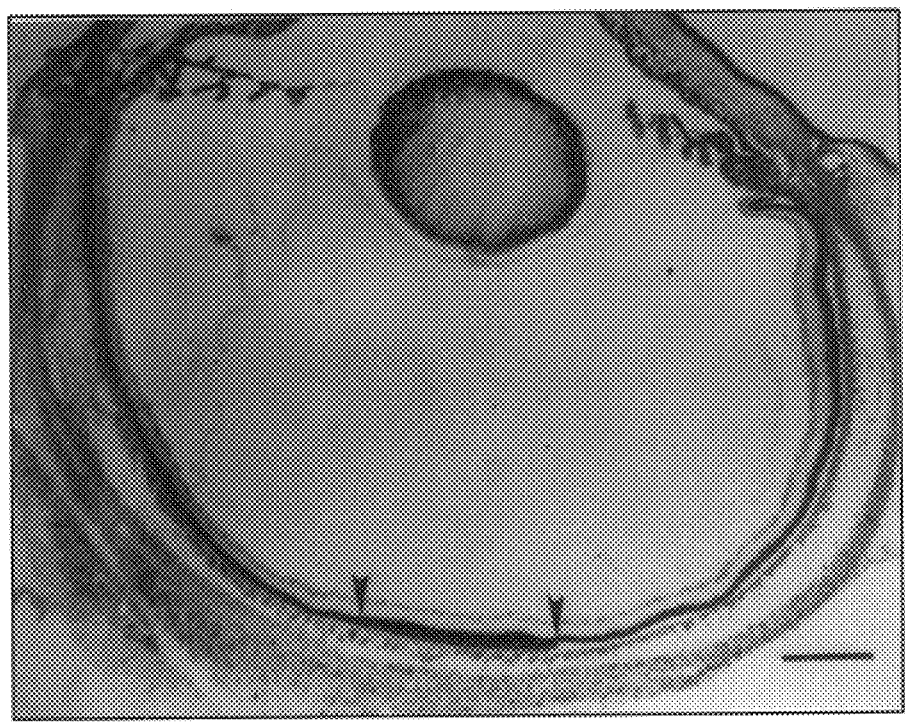
FIG. 22 is a photograph of donor photoreceptors transplanted at the posterior pole of the recipient eye as set forth in Example 1.
Figure 23:
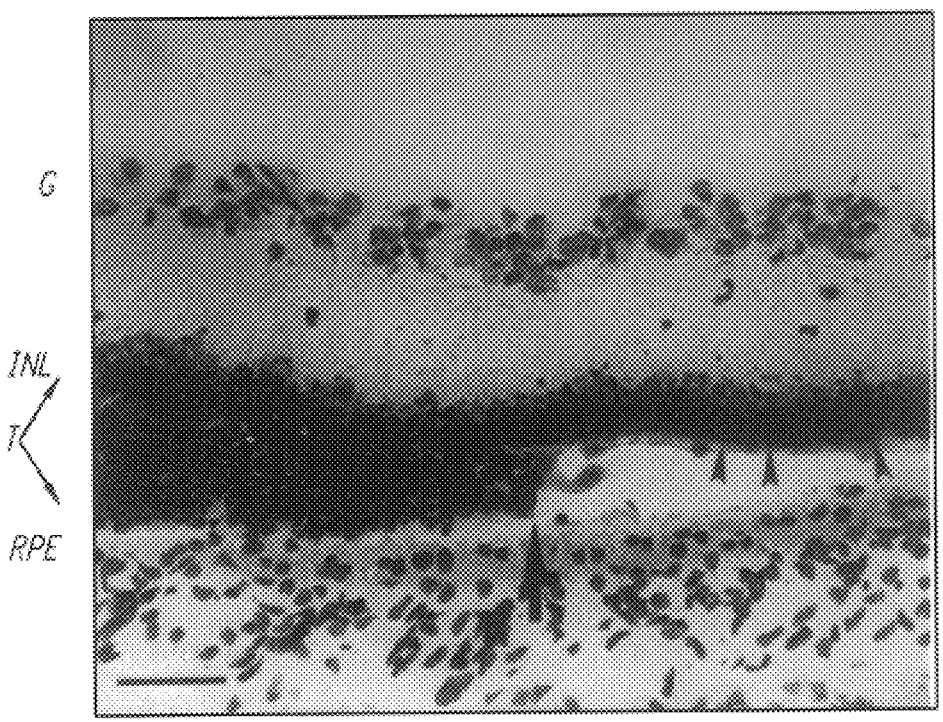
FIG. 23 shows the interface between the transplant and the adjacent retina devoid of outer nuclear layer as set forth in Example 1.

Cryostat sections made at 4 weeks post-transplantation are shown in FIGS. 22–24. FIG. 22 is a low-power photomicrograph showing the location of the photoreceptor transplant (between arrowheads) at the posterior pole of the host eye Bar=0.5 mm. FIG. 23 is a higher-power photomicrograph showing the interface between the transplant and the adjacent retina devoid of outer nuclear layer. Arrows indicate the extent of the transplant (T). Arrowheads indicate three possible residual photoreceptors that survived constant illumination. Note their fusiform shape contrasts with the rounder, more normal shape of the transplanted photoreceptors. H & E stain. Bar=100 μm. FIG. 24 is a FITC fluorescent micrograph of antibody Ret P-1 specific for opsin in a section adjacent to that shown in FIG. 23. Arrows indicate the extent of the transplant. Transplanted cells are labeled for opsin indicating they are photoreceptors. Some nonspecific fluorescence is evident adjacent to the transplant. Bar=100 μm.

Cryostat sections made at 3 weeks post-transplantation are shown in FIGS. 25A–C. FIG. 25A is a H & E-stained photomicrograph of a transplant and host retina. Note the cell-sparse layer that resembles the outer plexiform layer interposed between the host retina and the transplant. FIG. 25B is a diI fluorescent photomicrograph of adjacent section. Transplanted photoreceptors show diI fluorescence, identifying them as donor tissue. FIG. 25C is a FITC fluorescent micrograph of antibody RET-P1 in a section adjacent to that shown in FIG. 25A. Transplanted cells are labeled for opsin, indicating that they are photoreceptors. Bar=50 μm.

Results

By using the transcorneal approach, it was found that the positioning of the photoreceptor layer between the host's retina and the adjacent epithelial and choroidal tissue layers of the eye could be accomplished while minimizing the vascular damage and subsequent bleeding into the eye. In addition, it was found that this approach does not appear to disrupt the integrity of the retina, which reattaches to the back of the eye with the transplanted photoreceptors interposed between the retina and the RPE. As shown in FIGS. 21–24, retinal reattachment appears to be facilitated in the immediate area of the transplant. (The "T" indicates transplanted sheets of photoreceptor cells). Using this insertion method, it was possible to position the photoreceptors at the posterior pole of the retina (FIG. 22).

To determine the viability of the transplanted photoreceptors, cryostat sections (20 μm) were made from both the blinded eye (control) and the eye receiving the photoreceptor transplant at 2, 4, or 6 weeks after transplantation. It was found that the photoreceptors survived transplantation at all times tested (36 out of 54 transplants). In most instances, the surviving transplant approximated its size at the time of transplantation. More importantly, there was no apparent reduction in transplant size with longer survival times, suggesting that the transplants were stable.

As a control, the contralateral eyes that did not receive a photoreceptor transplant were examined. In these eyes, the retinas possessed very few residual photoreceptors located adjacent to the outer plexiform layer and the RPE. However, these residual cells were abnormal in their appearance, having flattened, pyknotic cell bodies instead of the rounded cell bodies of normal photoreceptors. Furthermore, the residual photoreceptors did not form an outer nuclear layer composed of columnarly stacked cell bodies, but instead were found in isolation, or at most appear as a single or double layer of cells (see FIG. 23) located mainly in the peripheral retina.

The transplanted cells were easily distinguished from the residual photoreceptors by a number of parameters. First, they were found in discrete patches and have the characteristic columnar stacking arrangement of up to about 12 cell bodies that is characteristic of photoreceptor cells in the outer nuclear layer of the normal retina. They did not have the flattened appearance of the residual native photoreceptors, but instead have the round, nonpyknotic cell body typical of normal transplanted cells. Furthermore, the transplanted photoreceptors can form rosette configurations, a characteristic of transplanted and cultured retina while residual photoreceptors were not found in these configurations.

To eliminate the possibility that the surgical procedure in some manner induced the regeneration of native photoreceptors, sham operations were performed. All procedures were performed as with the photoreceptor transplants except that no photoreceptors were attached to the inserted gelatin slab. While the retina reattached to the back of the eye, in no instance were patches of photoreceptors found.

To positively identify the photoreceptor patches in experimental animals as transplanted tissue, the donor outer nuclear layer was labeled with the fluorescent marker diI prior to the transplantation. As shown in FIG. 25B, the photoreceptor patches were fluorescently labeled while the host retina did not show diI fluorescence.

To confirm that the transplants consisted of photoreceptors, a monoclonal antibody specific for opsin, RET-P1 was used. As opsin is found only in photoreceptors, any cell showing labeling for opsin was, therefore, identified as a photoreceptor. As can be seen in FIGS. 24 and 25C, the transplanted cells stain intensely for opsin whereas other retinal cells are unstained. Positive staining for opsin not only identifies these cells as photoreceptors but indicates that these cells are still capable of producing the protein moiety of visual pigment. Retina adjacent to the region of the transplant shows only a few isolated photoreceptor cell bodies (FIG. 23) that do not stain for opsin (FIG. 24) suggesting that they are cones. Their lack of opsin staining, as well as their location and appearance in H & E-stained material, confirms that these cells are the host's residual photoreceptors (FIG. 23).

Harvesting the photoreceptor layer from the neonatal retina does not appear to disrupt tissue organization. Once transplanted, the photoreceptor layer maintained its characteristic columnar arrangement of cell bodies for all survival times examined, thus forming a new outer nuclear layer within the host's retina. In some cases, strict polarity was lost and the rosettes were formed. By light microscopy, the new layer appeared to be attached to the host's outerplexiform layer (FIGS. 22 and 25A). This layer normally is the site of synaptic contact between the photoreceptors and the retina.

EXAMPLE 2

The procedures of Example 1 were repeated except as noted. Substituted for the Sprague-Dawley rats were the rd mouse and the RCS rat which are afflicted with inherited retinal degeneration. In the rd mouse it is thought that the deficit resides in the photoreceptor whereas in the RCS it is thought that the deficit resides in the pigment epithelium. In these animals, almost all photoreceptors are eliminated while the remaining retina is preserved; either the rd mouse or the RCS rat were blinded by constant illumination as set forth in Example 1. The rd mouse and the RCS respectively received transplants of immature (7–8 day old mouse or rat) and mature rat photoreceptors.

rd Mouse

The transplantation technique was adapted to the smaller size of the mouse eye. This modification allowed sheets of intact outernuclear layer to be transplanted to the subretinal space of the mouse eye. Neonatal (8 days old) photoreceptors were transplanted from rd control mice to the subretinal space of adult rd mice. Survival times were for 2 weeks to 3 months. At all survival times, it was found that the transplanted photoreceptors survived, becoming physically attached to the outer portion of the host retina and stained positive for opsin. In addition, the host retina became reattached to the pigment epithelium.

In the rd mouse almost all photoreceptors are eliminated by day 21. It was found that photoreceptors from a non-dystrophic congenic control mouse can be transplanted to their appropriate site within the adult rd mouse eye that lacks photoreceptors. These transplanted photoreceptors were found to survive for as long as tested (3 months). This length of time is significant since photoreceptors of the rd mouse show signs of degeneration after about 2 weeks and are almost completely eliminated after 3 weeks. The survival of transplanted photoreceptors from congenic normal donors to the adult rd mouse within the rd mouse supports findings that indicate that the deficit within the rd mouse which causes the degeneration of photoreceptors is endogenous to the rd photoreceptors themselves.

RCS Rat

Photoreceptors from 7 to 8 day old RCS controls (normal) were transplanted to the subretinal space in the eye of adult (3 month old) RCS rats. A two month survival period was allowed because in this time period almost all host photoreceptors degenerate in the RCS rat. It was found that the grafted photoreceptors survive transplantation to the subretinal space of the RCS rat and show histotypic as well as immunological characteristics of normal photoreceptors. In addition, it was found that transplanted photoreceptors survive within their homotopic location in the RCS rat whereas the RCS's own photoreceptors do not.

Results

While it has been found that the transplanted photoreceptors survive, produce opsin, and apparently integrate with the recipient retina, they do not appear completely normal in that the number of outer segments is reduced. However, photoreceptors lacking outer segments are still capable of phototransduction as indicated in Pu et al., *J. Neorosci.*, 4:1559–1576, 1984. The relative scarcity of outer segments has also been noted in retina transplanted to the tecum. These retina have been shown to be functional as indicated in Simon et al., *Soc. Neorosci. Abstr.*, 10:668, (1984).

Conventional reasoning attributes the observed deficiency in outer segments to be the possible consequence of the lack of appropriate apposition of the RPE to the photoreceptors as indicated in LaVail et al., (1971), noted above. However, it has been found that RPE is present and in apparently normal apposition to the photoreceptors, thus, the scarcity of outer segments here would not appear to be related to inadequate contact between photoreceptor and RPE. The failure of outer segment growth in the presence of photoreceptor apposition to the RPE has also been seen following retinal reattachment as reported by Anderson et al., *Invest. Opthalmol.* Vis, Sci. 24:906–926, 1983.

EXAMPLE 3

The procedures of Example 1 were repeated except as noted.

Donor photoreceptors were originally harvested at the earliest ontogenetic time in which the photoreceptors could be isolated from other portions of the retina (7–8 days old) since it is generally believed that more embryonic and undifferentiated neural tissue survives transplantation far better than more mature and differentiated tissue. To determine the effect of developmental age on photoreceptor survival and ability to integrate with the host retina, photoreceptors were subsequently transplanted from 8, 9, 12, 15 and 30 day old rats into light damaged adults. These show progressive development and maturation of the photoreceptors including mature outer segments (at 15 and 30 days).

Figure 26A:
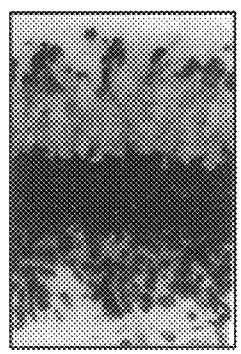
FIG. 26 comprises two micrograph panels, in A, transplant of nature rat photoreceptors to adult light damaged recipient or host, and in B, transplant of human photoreceptor from adult donor to adult light damaged rat host or recipient as set forth in Example 4.

Using the same criteria as in Example 1, it was found that for all ages tested the transplants survived for as long as examined (2 months) and integrated with the host retina. FIG. 26, panel A, is a photograph of a transplant of mature photoreceptors (30 day old donor) to adult light damaged host. (T, Transplant). 120X. These observations suggest that photoreceptors have characteristics that differ from other neural tissue that permits them to be transplanted when they are essentially mature while other neural tissue must be at a very immature stage for successful transplantation to occur.

EXAMPLE 4

The procedures of Example 1 were repeated except as noted. Photoreceptors were taken from the retina of donated human eyes (obtained from the Missouri Lions and St. Louis Eye Banks) following corneal removal. A portion of the retinas were tested for viability by dye exclusion with trypan blue and didansyl cystine staining. The photoreceptors excluded dye and appeared to be in good condition. Hosts were adult albino rats (immune-suppressed with cyclosporin A or immune-competent) exposed to constant illumination.

Figure 26B:
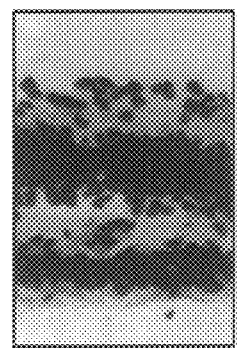

With immune-suppression successful transplants were seen at all survival times so far examined (one and two weeks; five of nine cases), showing apparent physical integration with the host retina and maintaining morphological features of the outer nuclear layer as illustrated in FIG. 26B which shows a transplant of human photoreceptors from adult donor to adult light damaged rat host. (T, transplant). 120X.

The transplants stained positive for antiopsin antibody RET-P1, identifying the transplanted cells as photoreceptors and further indicating that they are still capable of producing visual pigment. In contrast, transplants to immune-competent hosts showed signs of rejection within one week of transplantation. Sham operated animals showed no repopulation of the host retina with photoreceptors.

The procedures of Example 1 were repeated except as noted.

The 2DG functional mapping technique developed by Sokoloff et al., *J. Neurochem.* 28:897–916 (1977) allows the measurement of the relative levels of neural activity for a given stimulus condition. For this reason, the 2DG technique appeared to be an appropriate method of assessing the functional characteristics of the transplant and its ability to activate the light damaged retina.

Accordingly, patterns of 2DG uptake in the normal retina were compared to that seen in the light-damaged retina, with and without a photoreceptor transplant. These comparisons were made under two different visual stimulus conditions: 1) darkness and 2) strobe flicker at 10z. FIG. 27 illustrates the results of these comparisons. H&E stained retina with corresponding 2-deoxyglucose autoradiographs. A and B normal retina. Sections cut slightly tangentially to expand retinal layers. C. Dystrophic (light-damaged) retina plus photoreceptor transplant (T) left of arrow. Black and white lines at left on 2DG autoradiograph bracket lower 2DG uptake in inner plexiform and ganglion cell layers. D. Dystrophic retina plus photoreceptor transplant left of arrow. ONL; outer nuclear layer, T; transplant, DYST; dystrophic, Bar=0.5 mm.

As shown in panel 27A, in darkness 2DG was preferentially taken up in the outer portion of normal retina (photoreceptors and possibly the inner nuclear layer). As shown in panel 27B, with strobe flicker stimulation 2DG uptake extends through the thickness of the normal retina. These patterns of 2DG uptake are in good agreement with the known physiological characteristics of the retina.

The outer retina might be expected to show high 2DG uptake in the dark since photoreceptors, horizontal and some bipolar cells are maximally depolarized in this situation. As strobe flicker is a strong stimulus for the retina including the amacrine and retinal ganglion cells, 2DG uptake across the entire retina is also to be expected. It therefore appears that the 2DG uptake pattern in normal retina reflects relative degrees of neural activity or neural depolarization, and therefore is a useful indicator of neural activity in the retina as it is in other areas of the nervous system.

Figure 27A:
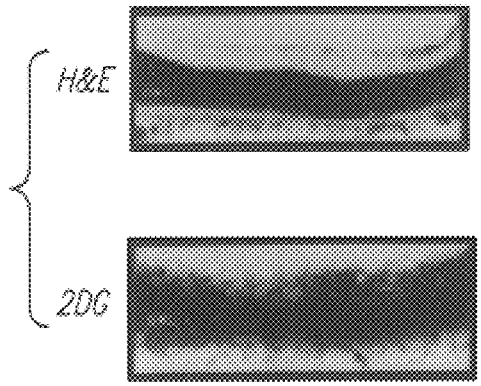
FIGS. 27a, 27b, 27c, 27d are $^{14}$C 2-deoxyglucose (2DG) autoradiographs, DYST-dystrophic, TRANS-transplant as set forth in Example 5.
Figure 27B:
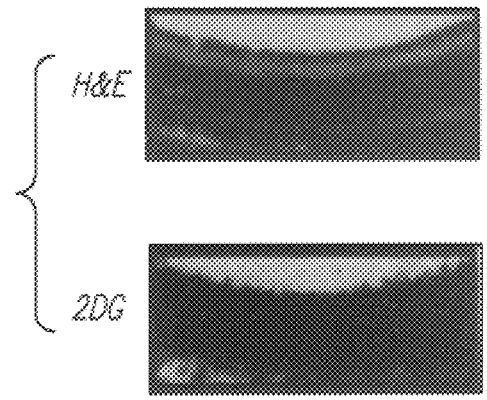
Figure 27C:
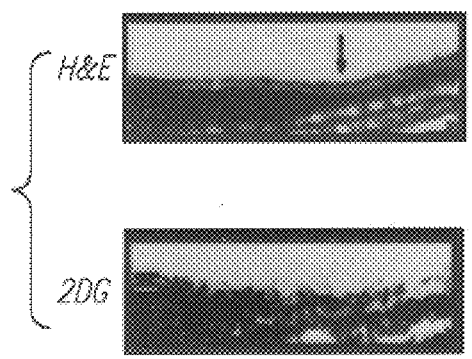
Figure 27D:
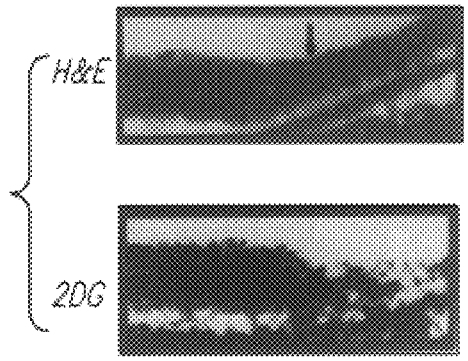
Figure 28A:
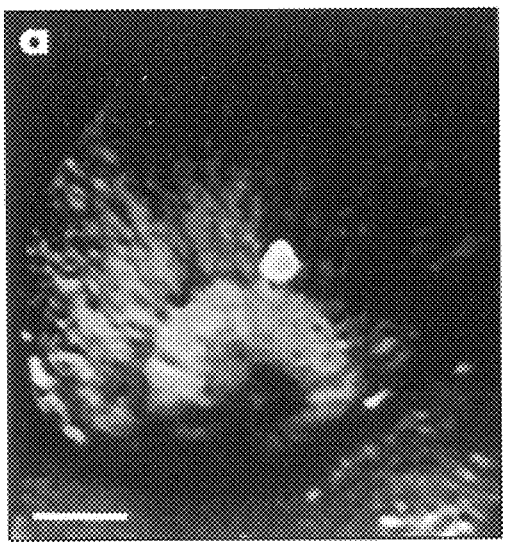
FIGS. 28a, 28b, 28c and 28d are a is series of photographs showing pupillary reflex to light as set forth in Example 9.
Figure 28B:
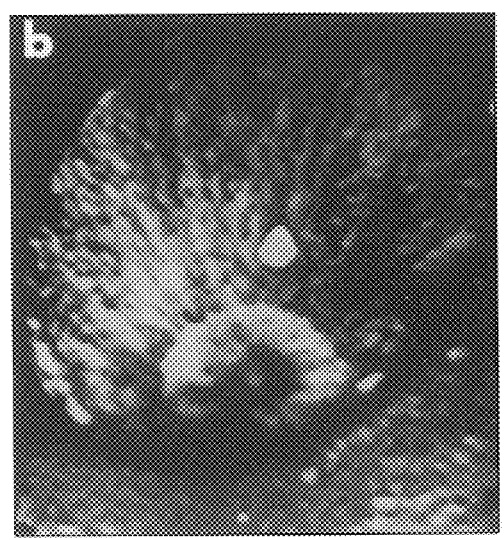
Figure 28C:
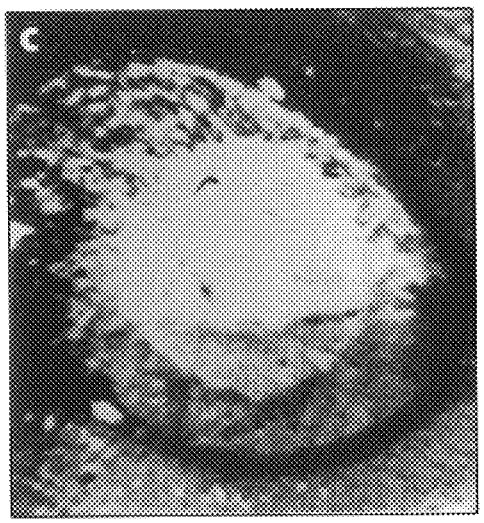
Figure 28D:
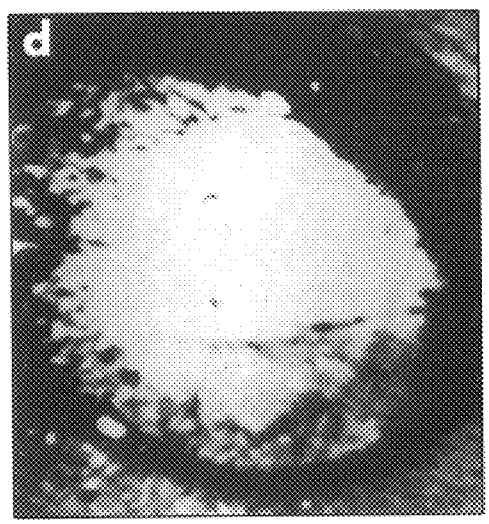

In the light-damaged retina which received a photoreceptor transplant, the pattern of 2DG uptake was also dependent on the stimulus conditions. In the dark, preferential uptake of 2DG was limited to the photoreceptor transplant and the adjacent host inner nuclear layer while relatively lower uptake was present in the host's inner plexiform and ganglion cell layers. However, in the strobe flicker condition, high 2DG uptake is present in the transplant and, in addition, extended through the thickness of the host's retina—but only in the area of the photoreceptor graft (FIG. 27D). Adjacent host retina which did not receive the photoreceptor transplant shows relatively low 2DG uptake.

In darkness, both the normal retina and the light-damaged retina receiving the photoreceptor transplant show relatively high uptake of 2DG in the photoreceptor and inner nuclear layers. The similarity in the relative uptake patterns between these cases suggests that the transplanted photoreceptors may have similar functional characteristics as normal photoreceptors (i.e., they depolarize in the dark and are capable of inducing a sustained depolarization of some cells in the host's inner nuclear layer).

In strobe flicker, the light-damaged retina receiving the photoreceptor transplant showed high 2DG uptake through the entire thickness of the retina much like that seen in the normal retina under the same stimulus condition. Adjacent light-damaged retina that did not receive a photoreceptor transplant showed relatively low 2DG uptake. These comparisons show that the pattern of 2DG uptake in the light-damaged retina approximates that seen in the normal retina only in areas of the host retina that received photoreceptor grafts. Adjacent areas of the host retina show relatively low levels of 2DG uptake in both stimulus conditions. The similarity in the 2DG uptake patterns between the light-damaged retina following photoreceptor grafting and the normal retina in both stimulus conditions suggests that the photoreceptor transplant is capable of light-dependent activation of the light-damaged retina.

EXAMPLE 6

The procedures of Example 1 were repeated except as noted.

While activation of the host retina by the transplanted photoreceptors was seen with deoxyglucose mapping the nature of this activation was unclear. Specifically, does such activation represent a nonsynaptic modulation of neurotransmitter release by the transplanted photoreceptors or are the transplanted cells forming synapses with elements of the host retina?

To address this issue, the ultrastructure of the reconstructed retina was investigated. Following appropriate survival times, animals were euthanized by overdose and immediately enucleated. Control and experimental eyes for light microscopy were fixed overnight in Bouin's solution. Following dehydration and clearing, the tissue was embedded in paraffin. Sections were cut on a rotary microtome. Eyes destined for plastic embedment were fixed for 2 hours in buffered 2.5% glutaraldehyde. After ½ hour of aldehyde fixation, the anterior segment and lens were removed to facilitate penetration of the fixative. Following primary fixation, eyes for light microscopy were processed further for methacrylate embedding. Two to 5 $\mu$m sections were cut on a rotary microtome using glass "Ralph" knives. In eyes for ultrastructural analysis, the area receiving the transplant was localized using the DiI label and excess tissue was trimmed before osmium postfixation. Following dehydration and clearing, the tissue was embedded in Epon/Araldite (Mollenhauer, 1964). Blocks were surveyed by staining semithin sections with toluidine blue. When the transplant was located, thin sections were cut and stained with uranyl acetate and lead citrate for examination on the EM.

A new outer plexiform-like layer was visible at the interface of the transplanted ONL and the host inner nuclear layer. Ribbon synapses were evident within this OPL. These synapses are characteristic of those formed by rod photoreceptors, with an electron dense ribbon surrounded by a cluster of vesicles. Ribbon synapses are found only rarely in control light-damaged retina. In addition to ribbon synapses, the transplanted photoreceptors also display inner segments, connecting cilia, and outer segment membranes. These results suggest that synaptic connections between transplanted photoreceptors and host cells were made indicating that the light-dependent activation may, at least in part, be synaptically mediated.

EXAMPLE 7

The procedures of Example 1 were repeated except as noted.

The functional capabilities of the transplanted photoreceptors and reconstructed retina was ascertained by recording visually evoked cortical potentials ("VEP"). To record the VEP, animals were implanted with stainless-steel screw electrodes embedded in the skull. The active electrodes were placed 2 mm anterior to lambda (bilaterally), and referred to a second electrode placed anterior to bregma. Both electrodes were placed 2 mm lateral to the midline and positioned on the dura. A third screw was placed above the nasal cavity to serve as a ground electrode.

Responses of the VEP were elicited by strobe flash test stimuli generated by a GRASS PS-2 photostimulator directed toward one eye with the other eye covered by a patch. Responses were differentially amplified (GRASS P-15D preamp), displayed on a TECTRONIX #564 oscilliscope and then averaged by a MACINTOSH IIx computer using LABVIEW.

It was found that the reconstructed retina can produce a light-evoked electrical response in the visual cortex whereas the unreconstructed fellow eye showed little or no response to the same light stimulus.

EXAMPLE 8

The procedures of Example 1 were repeated except as noted.

With indications that neural activity is generated in the central nervous system by the photoreceptor transplant and the reconstructed retina the question arises at to whether this neural activity can be processed appropriately by the central nervous system to produce an appropriate behavioral response to the sensory stimuli. Previous studies have shown that neural transplants to the brain can restore appropriate behavioral activity (Bjorklund et al., *Neural Graftin g in the Mammalian CNS*. Elsevier, Amsterdam, 1985). Klassen and Lund *Proc. Natl. Acad. Sci.* USA 84: 6958–6960, 1987; and *Exp. Neurol.* 102: 102–108, 1988 have shown that neural transplants can restore the pupillary reflex mediated by intracranial transplantation of embryonic retinas thus showing that neural transplants consisting of sensory tissue are capable of mediating a behaviorally appropriate response to sensory stimulation.

Rats with dystrophic retinas received a photoreceptor transplant as described in Example 1. At various postsurgical time intervals (E.G., 2, 4 and 8 weeks, etc.) animals were anesthetized and held in a stereotaxic device. An infrared video camera was focused on the eye through an operating microscope and the eye illuminated with infrared light. To test for pupillary reflex, a light beam controlled by a camera shutter within the operating microscope was used. This light was focused on the eye. The pupillary response to the light at graded intensities (intensity of the light was controlled by neutral density filters) was recorded by video camera connected to a frame grabber system. The pupillary reflex was then analysed using automated imageprocessing software (ULTIMATE, GTFS, Inc.)

It was found that retinas reconstructed with photoreceptor transplants do in fact show a comparatively normal pupillary reflex to light (pupillary constriction) whereas the fellow dystrophic eye shows only a minimal reflex that is aberrant in form (pupillary dilation). The results are shown in FIG. 28*a*, 28*b*, 28*c* and 28*d*. Panels a and b are of the reconstructed retina. Panel a shows the iris at light onset whereas panel b shows the same eye at 5 seconds after light onset. Comparison of panel a to panel b shows a normal pupillary constriction mediated by light. Panels c and d show the fellow blinded eye that received sham surgery with panel c showing the iris at light onset and panel d showing the iris 5 seconds later. Comparison of panels c and d show an increase in pupil size with light. This response is aberrant in form and is characteristic of individuals suffering from severe retinal dystrophy of a photoreceptor type.

These results show that neural transplantation can reconstruct the host's own sensory end organ—in this case the eye—to restore an appropriate behavioral response (i.e., the pupillary reflex) to sensory stimuli. These results have profound significance for the feasibility of the restoration of vision by photoreceptor transplantation.

EXAMPLE 9

The procedures of Example 1 were repeated except as noted.

Photoreceptors were taken from mature macaque retina (animals sacrificed for other research) or the retina of donated human eyes (obtained from the St. Louis Eye Bank) using vibratome sectioning of the flat-mounted retina to isolate the intact outer nuclear layer. Hosts were mature macaque monkeys treated with iodoacetic acid (30 mg/kg given on 3 successive days) which selectively eliminates host photoreceptors in non-macular areas of the retina while leaving the remaining retina intact. This treatment did not compromise central vision and therefore maintained sight required for behavioral and physiologically important functions (e.g., locating of food and water, visually guided locomoter activities, grooming, maintenance of circadian rhythms).

The isolated outer nuclear layer was transplanted following a pars plana vitrectomy (a standard surgical technique) using a trans-scleral approach to the subretinal space. The photoreceptors were inserted under a focal retinal detachment induced by the formation of a subretinal bleb. The bleb was created by the infusion of ophthalmic balanced salt solution. The reconstructed retina was reattached to the back of the eye by pneumatic tamponade with the transplanted photoreceptors interposed between the retina and the underlying pigment epithelium. Daily injections of cyclosporin A and dexamethasone were made to suppress any possible transplant rejection.

It was found human photoreceptors survive transplantation to the non-human primate eye for as long as tested (2 weeks). These results indicate that mature human photoreceptors can be transplanted to the non-human primate eye. Since the non-human primate eye is almost identical to the human eye it is expected that human photoreceptors can be successfully transplanted to the human eye.

From the foregoing description those skilled in the art will appreciated that all aspects of the present invention are realized. The present invention provides an improved surgical instrument that is adapted to provide cell organization during transplantation of the photoreceptors. With the surgical instrument of this invention cell organization is maintained during photoreceptor, RPE, and choroidal transplantation while minimizing trauma to the transplanted tissues, the host eye and retina. It is believed that retina reattachment and subsequent substantially normal function of the reconstructed retina, in view of the transplant, is thereby facilitated. The present invention provides an improved surgical instrument that is constructed to allow relatively large expanses of the RPE, choroidea, and photoreceptor cell matrix or column to be transplanted to a sub-retinal space. Maintaining normal layer configuration of the photoreceptors, RPE, and choroidea allows these tissues to be transplanted to the appropriate position within the eye. The subsequent integration of the transplanted photoreceptors, RPE, and choroidea with the blinded retina facilitates reconstruction of the blinded retina. The present invention provides an improved surgical instrument that allows appropriate retinotopic positioning. The present invention provides an improved surgical instrument that protects photoreceptors from damage as the surgical device is positioned in the eye. The present invention provides a method of photoreceptor or retinal pigment epithelium isolation and transplantation that, maintains to the extent possible the normal organization of the outer nuclear layer and these other tissues. The present invention provides a method of cell and tissue isolation by which cells can be isolated without disruption of their intercellular organization. With the method of this invention retinal cells, such as retinal photoreceptors can be isolated without the disruption of the intercellular organization of the outer nuclear layer or other layer of the retina, RPE, and choroidea.

A number of features of the transplanted cells are that they are and remain alive; they produce opsin, important for phototransduction; they are functional (i.e., activated by light); and the transplanted photoreceptors activate a previously blinded retina in a light dependent fashion.

Attachment of retinal tissue to the gelatin substrate allows extended periods of in vitro culture of retinal tissues by: maintaining organization of tissue in culture; and allowing for a better viability of cultured tissue.

While a number of embodiments have been shown and described, many variations are possible. Photoreceptors can be transplanted to retina in which the host's or recipient's photoreceptors are lost by environmental (constant light) or inherited defects. (See: S. E. Hughes and M. S. Silverman (1988) in "Transplantation of retinal photoreceptors to dystrophic retina", *Soc. Neurosci. Abstr.*, 18: 1278.) Furthermore transplanted photoreceptor cells maintain basic characteristics of normal photoreceptor cells by producing opsin and maintaining an intercellular organization and apposition to the host retina that is similar to that seen in the normal outer nuclear layer. The surgical instruments may be larger for use in humans. Other approaches to the subretinal space may be used, e.g., trans-scleral, choroidal. Other substrates besides gelatin can be used, e.g. agar, agarose, in fact improved substrates could include factors that can be integrated into gelatin, for example, neurotrophic factors). It is believed that attachment to gelatin or equivalent substrates will allow prolonged in vitro culture, or cryogenic freezing, and similar storage, while allowing for the maintenance of tissue organization and viability. Finally, it is believed that other methods of attaching retina to substrate can be used, such as lectins, or photo-activated cross-linking agents.

It has been shown that this invention provides a method to isolate the intact photoreceptor layer. This is significant because it will be necessary to maintain tight matrix organization if coherent vision is to be restored to the retina comprised by the loss of photoreceptors. A surgical approach has been disclosed which minimizes trauma to the eye and allows controlled positioning of sheets of transplanted photoreceptors to their homotopic location within the eye. In addition these methods for transplantation and isolation of photoreceptors could be utilized to prepare and transplant other retinal layers so that selected populations of retinal cells can be used in other neurobiological investigations and clinical procedures. It is believed that these other retinal layers, once they are flattened, appropriately sectioned, and appropriately affixed to a stabilizing substrate or base, could be prepared for transplantation, storage (e.g., in vitro, cryogenic), or culturing similar to the methods described herein for photoreceptor layers.

The necessity for prompt re-vascularization typically limits the ability to transplant most neural tissue, but not photoreceptors. The photoreceptor layer of a retina and the ("RPE") is non-vascularized. Non-vascularized tissue shows the least amount of tissue rejection. Consequently, it is believed that genetically dissimilar photoreceptor cells may be transplanted in accordance with the present invention. Matching of host and donor histocompatibility antigens will probably b necessary for transplantation of the retinal pigment epithelium and choroidea.

Photoreceptors can be transplanted when developing or when mature. Not only can mature rat photoreceptors be transplanted, but mature photoreceptors from human donors can be transplanted as well. This is significantly different from neurons which must be immature in order to be transplanted. At present the reason for this difference is not known but has obvious importance for retinal and neural transplantation research in general.

Finally, transplanted photoreceptors activate the host's or recipient's dystrophic retina in a light dependent manner that closely resembles the activation pattern seen in normal retina.

In view of the above, it will be seen that the several objects of the invention are achieved and other advantages attained.

As various changes could be made in the above surgical instruments, compositions of matter and methods. Without, departing from the scope of the invention, it is intended that all matter contained in the above description or shown in the accompanying drawings shall be interpreted as illustrative and not in a limiting sense.

What is claimed:

1. A mammalian eye tissue graft, comprising mammalian eye tissue isolated from a donor eye laminated to a non-toxic and flexible support, said tissue consisting essentially of the outer nuclear layer of a retina, said outer nuclear layer having the same cellular organization as in the donor eye, wherein said support will not interfere with the viability of said tissue upon transplantation of the graft into a mammalian eye.

2. The eye tissue graft of claim 1, wherein said outer nuclear layer comprises photoreceptor cells.

3. The eye tissue graft of claim 1, wherein said support comprises gelatin.

4. The eye tissue graft of claim 2, wherein said support comprises gelatin.

5. A method of forming a mammalian eye tissue graft, comprising the steps of:

affixing mammalian eye tissue to a support, said eye tissue comprising cells, said eye tissue having a first portion and a second portion, wherein said second portion is affixed to said support;

removing said first portion without altering the organization of said cells forming said second portion so as to form a graft comprising at least part of said second portion affixed to at least part of said support, said support being non-toxic and flexible, said graft being capable of transplantation into a host eye, wherein said first portion comprises cells found in the inner nuclear layer of a retina, and said second portion comprises photoreceptor cells.

6. A mammalian eye tissue graft, comprising mammalian eye tissue isolated from a donor eye laminated to a non-toxic and flexible support, said eye tissue comprising at least one layer of cells found in tissue selected from the group consisting of the outer nuclear layer of a retina, retinal pigment epithelium, and choroidal tissue, said cells comprising said isolated layer having the same organization as in the donor eye, wherein the inner nuclear layer of the retina is substantially absent from said graft, said support will not interfere with the viability of said isolated tissue upon transplantation of the graft into a host eye, and said graft can be transplanted so that said cells will have the same polarity with respect to the retina in the host eye as said cells had in the donor eye.

7. The graft of claim 6, wherein said isolated eye tissue comprises photoreceptor cells.

8. The graft of claim 6, wherein said support comprises gelatin.

9. The graft of claim 7, wherein said support comprises gelatin.

10. A method of forming a mammalian eye tissue graft for transplantation to a host eye, comprising the steps of:

affixing mammalian eye tissue from a donor eye to a support, said eye tissue comprising cells found in tissue selected from the group consisting of retinal tissue, retinal pigment epithelium, and choroidal tissue, said eye tissue having a first portion and a second portion, wherein said second portion is affixed to said support;

removing said first portion without altering the organization of the cells forming said second portion so as to form a graft comprising at least part of said second portion affixed to said support, said support being non-toxic and flexible, said graft being capable of transplantation into a host eye, wherein said second portion comprises cells found in tissue selected from the group consisting of the outer nuclear layer of the retina, retinal pigment epithelium, and choroidal tissue, wherein said support will not interfere with the viability of said isolated tissue upon transplantation of the graft into a mammalian eye, and said graft can be transplanted to the subretinal space of a host eye so that said cells comprising said graft will have the same polarity with respect to the retina in the host eye as said cells had in the donor eye.

11. The method of claim 10, wherein said eye tissue comprises retinal tissue having an inner nuclear layer and an outer nuclear layer, and said first portion comprises said inner nuclear layer, and said second portion comprises said outer nuclear layer.

12. The method of claim 11, wherein said support comprises gelatin, and said second portion comprises photoreceptor cells.

13. A method of forming a mammalian eye tissue graft and transplanting the graft to a host eye, comprising the steps of:

affixing mammalian eye tissue from a donor eye to a support, said eye tissue comprising cells found in tissue selected from the group consisting of retinal tissue, retinal pigment epithelium, and choroidal tissue, said eye tissue having a first portion and a second portion, wherein said second portion is affixed to said support;

removing said first portion without altering the organization of the cells forming said second portion so as to form a graft comprising at least part of said second portion affixed to said support, said support being non-toxic and flexible, said graft being capable of transplantation into a host eye, wherein said second portion comprises cells found in tissue selected from the group consisting of the outer nuclear layer of the retina, retinal pigment epithelium, and choroidal tissue, wherein said support will not interfere with the viability of said isolated tissue upon transplantation of the graft into a mammalian eye; and transplanting said graft beneath the retina of a host eye so that said cells will have the same polarity with respect to the retina in the host eye as said cells had in the donor eye.

14. The method of claim 13, wherein said second portion comprises photoreceptor cells.

15. The method of claim 14, wherein said support comprises gelatin.

* * * * *